(12) United States Patent
Smith et al.

(10) Patent No.: US 11,969,537 B2
(45) Date of Patent: Apr. 30, 2024

(54) MEDICAL WASTE FLUID COLLECTION AND DISPOSAL SYSTEM

(71) Applicant: DORNOCH MEDICAL SYSTEMS, INC., Riverside, MO (US)

(72) Inventors: Larry C. Smith, Shawnee, KS (US); Jeffery J. O'Bryan, Leawood, KS (US); Craig B. Schmidt, Lenexa, KS (US); Lawrence E. Guerra, Mission, KS (US)

(73) Assignee: Dornoch Medical Systems, Inc., Riverside, MO (US)

( * ) Notice: Subject to any disclaimer, the term of this patent is extended or adjusted under 35 U.S.C. 154(b) by 375 days.

(21) Appl. No.: 17/165,206

(22) Filed: Feb. 2, 2021

(65) Prior Publication Data
US 2021/0154375 A1 May 27, 2021

Related U.S. Application Data

(62) Division of application No. 15/223,254, filed on Jul. 29, 2016, now Pat. No. 10,940,242.
(Continued)

(51) Int. Cl.
*A61M 1/00* (2006.01)

(52) U.S. Cl.
CPC .............. *A61M 1/73* (2021.05); *A61M 1/60* (2021.05); *A61M 1/63* (2021.05); *A61M 1/743* (2021.05);
(Continued)

(58) Field of Classification Search
CPC .......... A61M 1/60; A61M 1/63; A61M 1/631; G02F 1/137; G02F 1/13756; F21V 14/003
See application file for complete search history.

(56) References Cited

U.S. PATENT DOCUMENTS 6,027,490 A  2/2000 Radford et al.
6,352,525 B1  3/2002 Wakabayashi
(Continued)

FOREIGN PATENT DOCUMENTS

EP    2359879 A2    8/2011
JP    2001017489 A  1/2001
(Continued)

OTHER PUBLICATIONS

"U.S. Appl. No. 15/223,254, Examiner Interview Summary dated Aug. 1, 2019", 3 pgs.
(Continued)

*Primary Examiner* — Adam Marcetich
(74) *Attorney, Agent, or Firm* — SCHWEGMAN LUNDBERG & WOESSNER, P.A.

(57) ABSTRACT

A medical waste fluid collection cart may include a container assembly and a suction tube having a lumen extending through the suction tube. The suction tube may communicate with the container to deposit waste fluid from a surgical site in the container. The container assembly may include a container, a base forming a bottom of the container, and a lid assembly. The base may include an interior surface defining a draining opening. The interior surface may extend along a ramped path toward the drain opening. The lid assembly may include a lid ring and a lid capable of engaging each other with a twist lock mechanism. The lid ring may engage the container and the lid may cover at least part of a central opening to the container. The container may have a window and a tinting assembly. The container assembly may have a vacuum level detection system.

20 Claims, 25 Drawing Sheets

Related U.S. Application Data

(60) Provisional application No. 62/199,539, filed on Jul. 31, 2015.

(52) U.S. Cl.
CPC ............... *A61M 2205/3389* (2013.01); *A61M 2205/3576* (2013.01); *A61M 2205/502* (2013.01); *A61M 2205/583* (2013.01); *A61M 2205/75* (2013.01); *A61M 2209/084* (2013.01); *A61M 2209/10* (2013.01)

(56) References Cited

U.S. PATENT DOCUMENTS

| | | |
|---|---|---|
| 7,134,620 B1 | 11/2006 | Lee |
| 8,172,832 B1 | 5/2012 | Gonzalez |
| 8,292,857 B2 | 10/2012 | Martini et al. |
| 8,366,694 B1 | 2/2013 | Jordan |
| 10,940,242 B2 | 3/2021 | Smith et al. |
| 2003/0143728 A1 | 7/2003 | Olivier |
| 2004/0065628 A1 | 4/2004 | Fout et al. |
| 2005/0215961 A1 | 9/2005 | Romano et al. |
| 2007/0135779 A1 | 6/2007 | Lalomia et al. |
| 2008/0004576 A1* | 1/2008 | Tanaka .................... A61F 5/451 604/326 |
| 2008/0316395 A1* | 12/2008 | O'Keeffe ............. C09K 19/544 349/88 |
| 2009/0012485 A1 | 1/2009 | Michaels et al. |
| 2009/0015740 A1* | 1/2009 | Sagitov ...................... B60J 3/04 349/16 |
| 2010/0052293 A1 | 3/2010 | Brooks et al. |
| 2010/0064558 A1* | 3/2010 | Pelfrey ................... G09F 23/02 40/447 |
| 2011/0170030 A1* | 7/2011 | Boote ....................... E06B 9/24 359/296 |
| 2011/0265889 A1* | 11/2011 | Tanaka .................... A61M 1/74 137/386 |
| 2011/0310318 A1* | 12/2011 | Kawagoe ............... G02B 30/24 349/13 |
| 2013/0001254 A1* | 1/2013 | Pelfrey ..................... G09F 9/35 222/173 |
| 2013/0281885 A1 | 10/2013 | Rowbottom et al. |
| 2014/0063046 A1* | 3/2014 | Jung ........................ G09G 5/02 345/592 |
| 2014/0138276 A1* | 5/2014 | Smith .................... B65D 79/00 206/459.1 |
| 2014/0177028 A1* | 6/2014 | Shrivastava ............ G09F 23/02 359/275 |
| 2014/0305897 A1* | 10/2014 | Lee ........................ H10K 59/30 215/11.1 |
| 2014/0320950 A1* | 10/2014 | Saxe ................... G02F 1/13318 359/296 |
| 2015/0190557 A1* | 7/2015 | Nobles ............... B65D 81/3876 220/737 |
| 2015/0224237 A1* | 8/2015 | Reasoner ............. A61B 5/6887 604/320 |
| 2016/0055303 A1* | 2/2016 | Keller ................. A61M 1/3496 210/85 |
| 2016/0061514 A1 | 3/2016 | Seo et al. |
| 2016/0074637 A1* | 3/2016 | Croizat ................. A61M 1/984 604/543 |
| 2016/0161780 A1* | 6/2016 | Van Oosten ............. E06B 9/24 349/16 |
| 2016/0208545 A1* | 7/2016 | Baba ........................ E06B 7/30 |
| 2016/0353934 A1 | 12/2016 | Shanmugam |
| 2017/0010218 A1* | 1/2017 | He ..................... G01N 21/9501 |
| 2017/0017100 A1* | 1/2017 | Liao ................. G02F 1/134309 |
| 2017/0028110 A1 | 2/2017 | Smith et al. |
| 2017/0216501 A1* | 8/2017 | Armstrong ............ A61M 1/918 |

FOREIGN PATENT DOCUMENTS

| | | |
|---|---|---|
| JP | 2002531877 A | 9/2002 |
| JP | 2009519757 A | 5/2009 |
| JP | 2010540193 A | 12/2010 |
| JP | 2018528043 A | 9/2018 |
| WO | WO-0152761 A1 | 7/2001 |
| WO | WO-2015055893 A1 | 4/2015 |
| WO | WO-2017023732 A1 | 2/2017 |
| WO | WO-2017060726 A1 | 4/2017 |

OTHER PUBLICATIONS

"U.S. Appl. No. 15/223,254, Final Office Action dated Jun. 14, 2019", 14 pgs.

"U.S. Appl. No. 15/223,254, Non Final Office Action dated Feb. 25, 2019", 9 pgs.

"U.S. Appl. No. 15/223,254, Non Final Office Action dated May 28, 2020", 21 pgs.

"U.S. Appl. No. 15/223,254, Notice of Allowance dated Nov. 4, 2020", 12 pgs.

"U.S. Appl. No. 15/223,254, Response filed May 23, 2019 to Non Final Office Action dated Feb. 25, 2019", 18 pgs.

"U.S. Appl. No. 15/223,254, Response filed Aug. 26, 2020 to Non Final Office Action dated May 28, 2020", 15 pgs.

"U.S. Appl. No. 15/223,254, Response filed Sep. 12, 2019 to Final Office Action dated Jun. 14, 2019", 18 pgs.

"U.S. Appl. No. 15/223,254, Response filed Nov. 5, 2018 to Restriction Requirement dated Sep. 7, 2018", 7 pgs.

"U.S. Appl. No. 15/223,254, Restriction Requirement dated Sep. 7, 2018", 7 pgs.

"Australian Application Serial No. 2016303432, First Examination Report dated Sep. 27, 2019", 4 pgs.

"Australian Application Serial No. 2016303432, Response filed Feb. 3, 2020 to First Examination Report dated Sep. 27, 2019", 15 pgs.

"Canadian Application Serial No. 2,994,152, Office Action dated Aug. 21, 2020", 3 pages.

"European Application Serial No. 16748017.7, Response filed Sep. 19, 2018 to Office Action dated Mar. 8, 2018", 13 pgs.

"International Application Serial No. PCT/US2016/044657, International Search Report dated Jan. 12, 2017", 7 pgs.

"International Application Serial No. PCT/US2016/044657, Invitation to Pay Add'l Fees and Partial Search Report dated Nov. 8, 2016", 7 pgs.

"International Application Serial No. PCT/US2016/044657, Written Opinion dated Jan. 12, 2017", 9 pgs.

"Japanese Application Serial No. 2018-525523, Notification of Reasons for Refusal dated Jun. 23, 2020", (W/ English Translation), 12 pgs.

"Japanese Application Serial No. 2018-525523, Response filed Sep. 4, 2020 to Notification of Reasons for Refusal dated Jun. 23, 2020", with English claims, 20 pages.

"New Zealand Application Serial No. 739592, First Examiner Report dated Dec. 6, 2019", 3 pgs.

U.S. Appl. No. 15/223,254, filed Jul. 29, 2016, Medical Waste Fluid Collection and Disposal System.

"Canadian Application Serial No. 2,994,152, Response filed Dec. 18, 2020 to Office Action dated Aug. 21, 2020", 18 pgs.

"International Application Serial No. PCT/US2016/044657, International Preliminary Report on Patentability dated Feb. 15, 2018", 11 pgs.

"Japanese Application Serial No. 2018-525523, Examiners Decision of Final Refusal dated Nov. 2, 2021", w/ English translation, 3 pgs.

"Japanese Application Serial No. 2018-525523, Final Notification of Reasons for Rejection dated Mar. 2, 2021", w/ English Translation, 5 pgs.

"Japanese Application Serial No. 2018-525523, Notification of Reasons for Refusal dated Aug. 23, 2022", w/ English translation, 5 pgs.

"Japanese Application Serial No. 2018-525523, Response filed Jan. 25, 2022 to Examiners Decision of Final Refusal dated Nov. 2, 2021", 18 pgs.

"Japanese Application Serial No. 2018-525523, Response filed May 26, 2021 to Final Notification of Reasons for Rejection dated Mar. 2, 2021", w/ English claims, 13 pgs.

(56) References Cited

OTHER PUBLICATIONS

"Japanese Application Serial No. 2018-525523, Response filed Sep. 13, 2022 to Notification of Reasons for Refusal dated Aug. 23, 2022", w/ English claims, 8 pgs.

* cited by examiner

MEDICAL WASTE FLUID COLLECTION AND DISPOSAL SYSTEM

CLAIM OF PRIORITY

This application is a divisional of U.S. application Ser. No. 15/223,254, filed Jul. 29, 2016, which claims the benefit of U.S. Provisional Patent Application Ser. No. 62/199,539, filed on Jul. 31, 2015, the benefit of priority of each of which is claimed hereby, and each of which is incorporated by reference herein in its entirety.

TECHNICAL FIELD

The present disclosure relates generally to systems and methods for collecting fluids during medical procedures and, in particular, to assemblies and systems for collecting waste fluids during medical procedures.

BACKGROUND

Biological fluids and other types of medical waste often must be collected during surgery or other medical procedures. This is typically accomplished using a medical waste fluid collection cart, which may be part of a medical waste fluid collection and disposal system. Such carts may include at least one suction canister where a vacuum port on the canister lid is connected to a source of vacuum via a hose or line. As a result, a vacuum is drawn on the interior of the canister. A second hose or line is connected to a "patient" suction port on the canister lid and is used to collect medical waste in the form of fluids and solids from the patient, which is stored in the canister. The medical waste collected in the canister may be drained through a drain in the canister. In some instances the drain may become clogged and/or a fluid level float valve within the canister may become obstructed with solid medical waste (e.g., blood clots, bone chips, etc.), which may require intervention. After collection, the medical waste and contaminated collection components, such as canister lids, and the like, must be disposed of in accordance with rules and regulations imposed by various government and regulatory organizations.

SUMMARY

The disclosure is directed to several alternative or complementary designs for, materials for, and methods of using, medical device structures, systems, and assemblies. Although it is noted that conventional medical waste fluid collection systems exist, there exists a need for improvement on those devices.

Accordingly, a medical waste fluid collection system may include a fluid collection cart, a container, and a lid assembly. The container may include a base enclosing a bottom end of the container. The base may include a drain opening and an interior surface that may extend along a ramped path toward the drain opening. The lid assembly may include a lid ring and a lid capable of removably engaging the lid ring via rotation of the lid relative to the lid ring. The lid ring may engage one or more of the container and the fluid collection cart.

A fluid waste container assembly may be utilized in a medical fluid collection system. The fluid waste container assembly may include a container, a base, and a lid assembly. The base may form a bottom for the container. The base may have an interior surface at least partially defining a drain opening. The lid assembly may provide selective access to an interior of the container. The container may have a window and a tinting assembly. The container assembly may have a vacuum level detection system.

In some cases, the fluid waste container assembly may be a medical waste fluid collection container assembly. The medical waste fluid collection container assembly may include a container, a base, and a lid assembly. The base may enclose a first end of the container. The lid assembly may include a lid ring and a lid capable of engaging the lid ring via a twist lock mechanism. The lid ring may have a central opening and may engage a second end of the container. The lid may be configured to cover at least part of the central opening when engaging the lid ring.

The above summary of some example aspects is not intended to describe each disclosed embodiment or every implementation of the claimed disclosure.

BRIEF DESCRIPTION OF THE DRAWINGS

The disclosure may be more completely understood in consideration of the following detailed description of various embodiments in connection with the accompanying drawings, in which.

Figure 1:
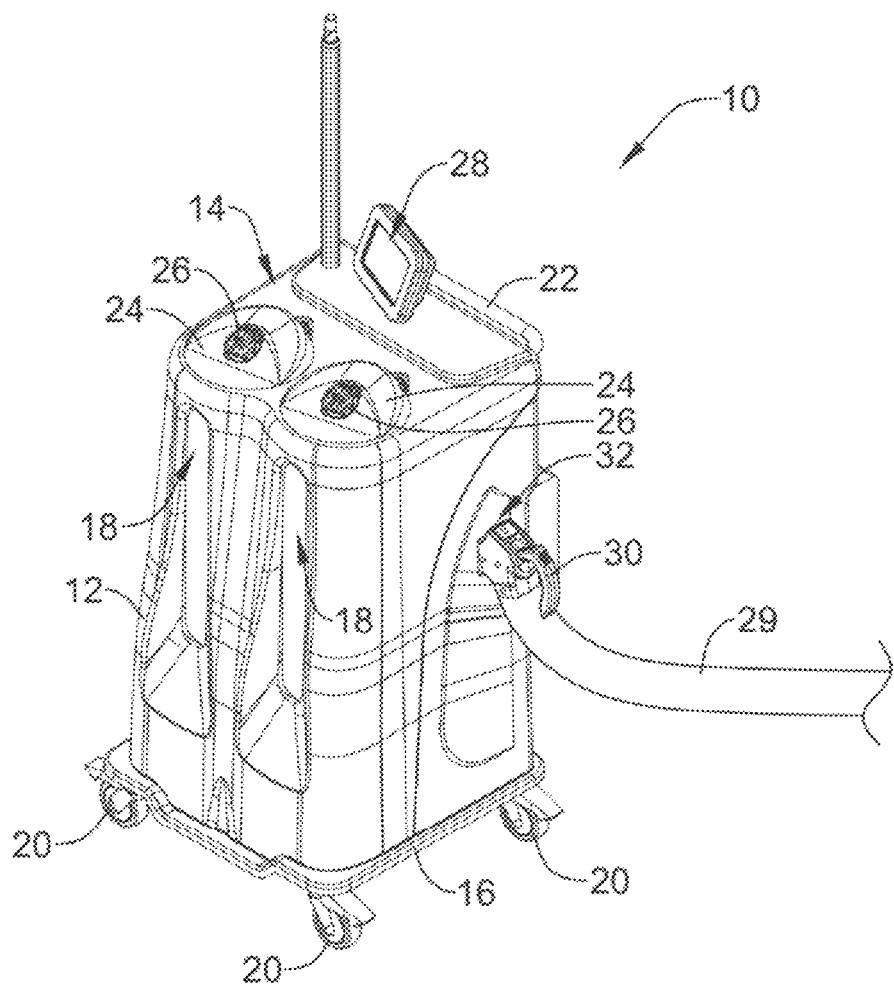
FIG. 1 is a perspective view of a medical waste fluid collection cart.

While the disclosure is amenable to various modifications and alternative forms, specifics thereof have been shown by way of example in the drawings and will be described in detail. It should be understood, however, that the intention is not to limit aspects of the claimed disclosure to the particular embodiments described. On the contrary, the intention is to cover all modifications, equivalents, and alternatives falling within the spirit and scope of the claimed disclosure.

DETAILED DESCRIPTION

For the following defined terms, these definitions shall be applied, unless a different definition is given in the claims or elsewhere in this specification.

All numeric values are herein assumed to be modified by the term "about", whether or not explicitly indicated. The term "about", when referring to numeric values, generally refers to a range of numbers that one of skill in the art would consider equivalent to the recited value (i.e., having the same function or result). In many instances, the term "about" may be indicative as including numbers that are rounded to the nearest significant figure. Additionally, or alternatively, the term "about" may generally refer to the area around an object or to a first object positioned at least partially around a second object.

The recitation of numerical ranges by endpoints includes all numbers within that range (e.g., 1 to 5 includes 1, 1.5, 2, 2.75, 3, 3.80, 4, and 5).

Although some suitable dimensions, ranges and/or values pertaining to various components, features and/or specifications are disclosed, one of skill in the art, incited by the present disclosure, would understand desired dimensions, ranges and/or values may deviate from those expressly disclosed.

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

The following detailed description should be read with reference to the drawings in which similar elements in different drawings are numbered the same. The detailed description and the drawings, which are not necessarily to scale, depict illustrative embodiments and are not intended to limit the scope of the claimed disclosure. The illustrative embodiments depicted are intended only as exemplary. Selected features of any illustrative embodiment may be incorporated into an additional embodiment unless clearly stated to the contrary.

FIG. 1 is a perspective view of a medical waste fluid collection cart 10 of or for use with a medical waste fluid collection and disposal system. An illustrative medical waste fluid collection and disposal system, which is not meant to be limiting in any way, is disclosed in, for example: U.S. patent application Ser. No. 12/245,966, now U.S. Pat. No. 8,292,857, filed on Oct. 6, 2008, entitled "MEDICAL WASTE FLUID COLLECTION AND DISPOSAL SYSTEM", the entirety of which is incorporated herein by reference for all purposes.

In some cases, the medical waste fluid collection cart 10 may include a housing 12 having a top 14, a bottom 16 and sides extending between the top 14 and the bottom 16. Positioned at least partially within the housing 12, or otherwise positioned on the cart 10, may be one or more fluid collection canisters or containers 18 (e.g., cylinders or other canisters or containers). While two containers 18 are shown in FIG. 1, the medical waste fluid collection cart 10 may include an alternative number of containers, for example, the medical waste fluid collection cart 10 may be configured to include one container, three containers, four containers, or another number of containers, if desired.

The housing 12 of the medical waste fluid collection cart 10 may be mounted on casters 20, for example. The casters 20 may be used to provide steering capability for the cart 10 providing the cart 10 with mobility to be moved to a desired location during use. The casters 20 may include a brake feature in some instances. The top 14 of the housing 12 may include a handle 22 to assist in moving and/or positioning the cart 10, if desired. As a result, the medical waste fluid collection cart 10 may be easily pushed to and from an operating room and/or other desired location.

In some cases, each of the containers 18 may be connected between a number of corresponding lids 24 and/or manifolds 26 (e.g., a manifold that may be connected to a lid of a container may provide fluid access to a container) via flexible tubing (not shown) to a vacuum source. The lids 24 and/or manifolds 26 may be constructed of molded plastic or other material and may be disposable.

The vacuum source (e.g., a vacuum pump) may be provided on the cart 10, or tubing may be connected to a vacuum source provided in the medical facility, such as a vacuum pump associated with wall suction provided in an operating room. A vacuum port on the lid 24 and/or manifold 26 may be provided with a filter, such as a hydrophobic filter, positioned in a compartment in the lid 24 and/or in the manifold 26.

Figure 2:
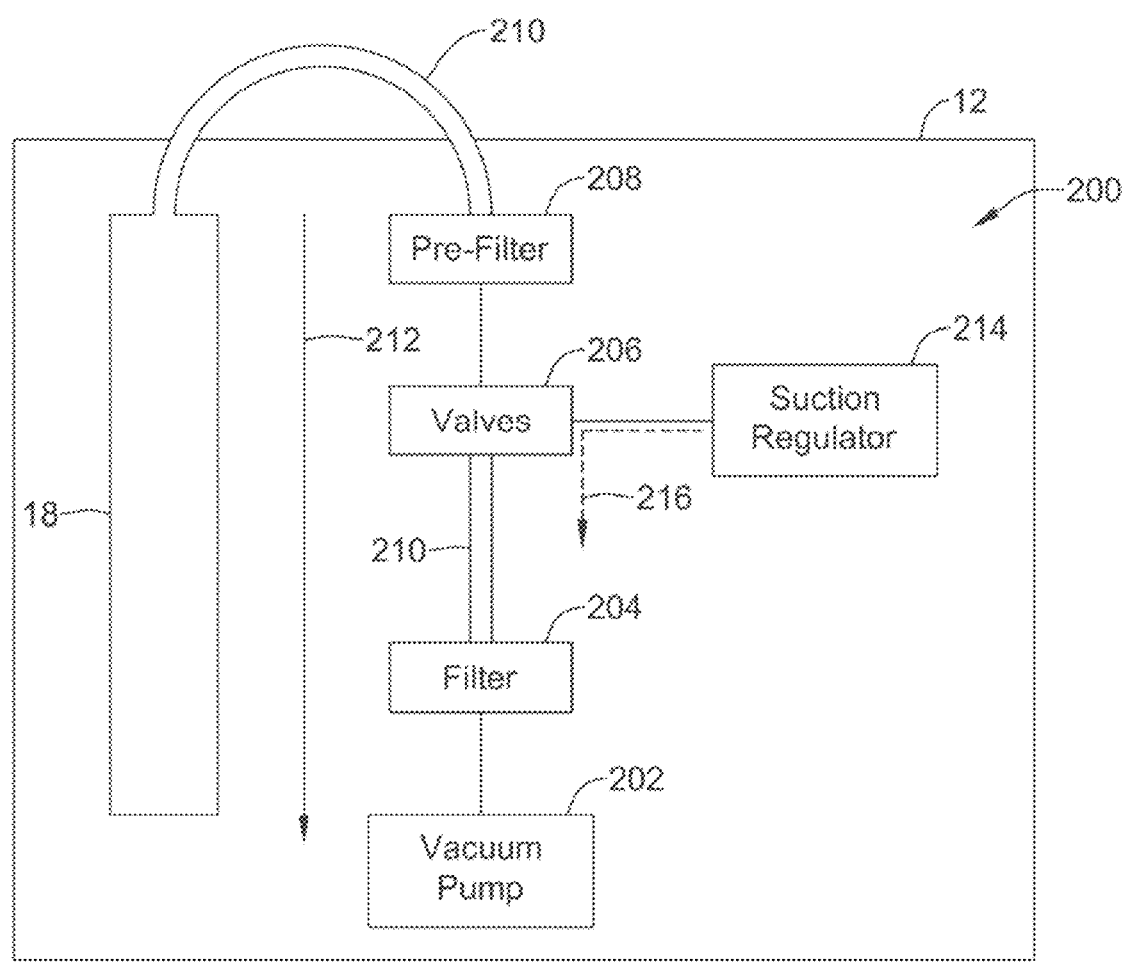
FIG. 2 is a schematic block diagram representation of an illustrative vacuum pump system.

FIG. 2 depicts a vacuum line system 200. The vacuum line system 200 may include one or more vacuum pumps 202, one or more filters 204, one or more valves 206, and one or more pre-filters 208. In response to actuation of a vacuum pump 202, a vacuum flow may flow from one or more containers 18 through a vacuum line 210 to, in the direction of arrow 212, the pre-filter(s) 208, to the valve(s) 206 (e.g., T-valves and/or other valves), through a further optional vacuum line 210, through the filter(s) 204, and out through the vacuum pump(s) 202. Vacuum lines 210 may be inserted between any device of the vacuum system 200, as desired.

In some cases, a suction regulator may be utilized in the vacuum line system 200 to regulate suction at a suction tube.

In one case of utilizing a suction regulator, the vacuum flow may be diverted to pass through a suction regulator in which the vacuum flow regulates suction pressure by constricting the flow path of the vacuum flow. In such a case, the vacuum flow may be required to pass through one or more bends to reach, flow through, and exit the suction regulator. Such bends and other restrictions may unnecessarily restrict the vacuum flow and reduce a suction pressure.

In an alternative configuration, as shown in FIG. 2, a suction regulator 214 may communicate with one or more valves 206 (e.g., a one direction T-valve or other valve) such that a vacuum flow does not pass directly through the suction regulator 214 (i.e., bypasses the suction regulator 214) and as a result, does not need to pass through one or more bends and/or restrictions within the suction regulator for a vacuum level to be regulated by a suction regulator. In such a configuration, the suction regulator 214 may be a bleed valve that may be actuated to bleed air into the vacuum flow in the direction of the dotted arrow 216. When actuated the suction regulator 214 may create a mix of air from the suction regulator 214 with the vacuum flow to reduce a vacuum flow velocity and a suction pressure at a suction tube in a calculated and intended manner without affecting an efficiency of the vacuum pump 202. The suction regulator 214 may be used with a single speed vacuum pump or a variable speed vacuum pump to adjust suction pressure, as needed.

A patient suction tube (e.g., a reusable or disposable suction tube) may be connected to a suction port on the lid 24 and/or the manifold 26, while one or more additional ports may be covered by caps or covers. The lid 24 and/or manifold 26 may include a tubing post or port for connection with the patient tubing. As a result, vacuum or suction is selectively drawn on each container so that fluids may be collected in the containers during the medical procedure via the suction tubing extending from the container to the patient. The suction and other functions of the medical waste fluid collection cart 10 may be controlled via a user interface 28 (e.g., a touch screen), which may include and/or may be communicably coupled to a controller.

Flexible tubing may be used to connect a lid 24 and/or manifold 26 to a vacuum port and a suction line or tube may connect to a suction port of the lid 24 or manifold 26, where each of the flexible tubing and the suction line or tube may include a lumen extending at least partially therethrough. In some cases, suction ports to which a suction tube is not attached, if any, may be covered with a cover or cap. In operation, a vacuum source may create a negative pressure within the container 18 to pass fluid removed from a surgical site through the lumen of the suction tube and deposit the removed fluid in the container 18.

After the medical waste fluid collection cart 10 is used in an operating room procedure, and fluids have been collected in one or more of the containers 18, the patient suction tubing may be removed from the container lids 24 and/or manifolds 26 and all suction ports for each container lid 24 or manifold 26 to which suction was applied may be covered with covers or caps. The medical waste fluid collection cart 10 may then be rolled to a position adjacent to the evacuation station for draining, washing, disinfecting, rinsing and return to a suction collection state.

The evacuation station may include a housing that contains a source of disinfection solution, pump, drainage system, and/or other components for draining, washing, and disinfecting the containers of the medical waste fluid collection cart 10. The evacuation station may communicate with the medical waste fluid collection cart 10 by way of a composite hose 29 and a coupler 30, for example. The coupler 30 may be received within a receptacle 32 of the medical waste fluid collection cart 10. Washing fluid from the evacuation station may be dispensed in the containers 18 with cleaning or spray nozzles (e.g., see spray nozzle 53 in FIG. 13) positioned in the containers 18 to wash and disinfect those containers 18.

When the draining, washing and disinfecting of the cart containers 18 is complete, the coupler 30 may be removed from the receptacle 32 on the medical waste fluid collection cart 10 so that the medical waste fluid collection cart 10 may again be rolled to an operating room for use. The coupler 30 permits a single connection to be made between the medical waste fluid collection cart 10 and the evacuation station. This simplifies and expedites connecting the medical waste fluid collection cart 10 to, and disconnecting the medical waste fluid collection cart 10 from, the evacuation station. When the medical waste fluid collection cart 10 and the evacuation station are connected using the coupler 30, one or more communication links may be used to permit a controller of the medical waste fluid collection cart 10 and a controller of the evacuation station to communicate so that the user can control both, including one or more of a draining operation, a washing operation and a disinfecting operation, via the user interface 28 or other user interface.

Figure 3:
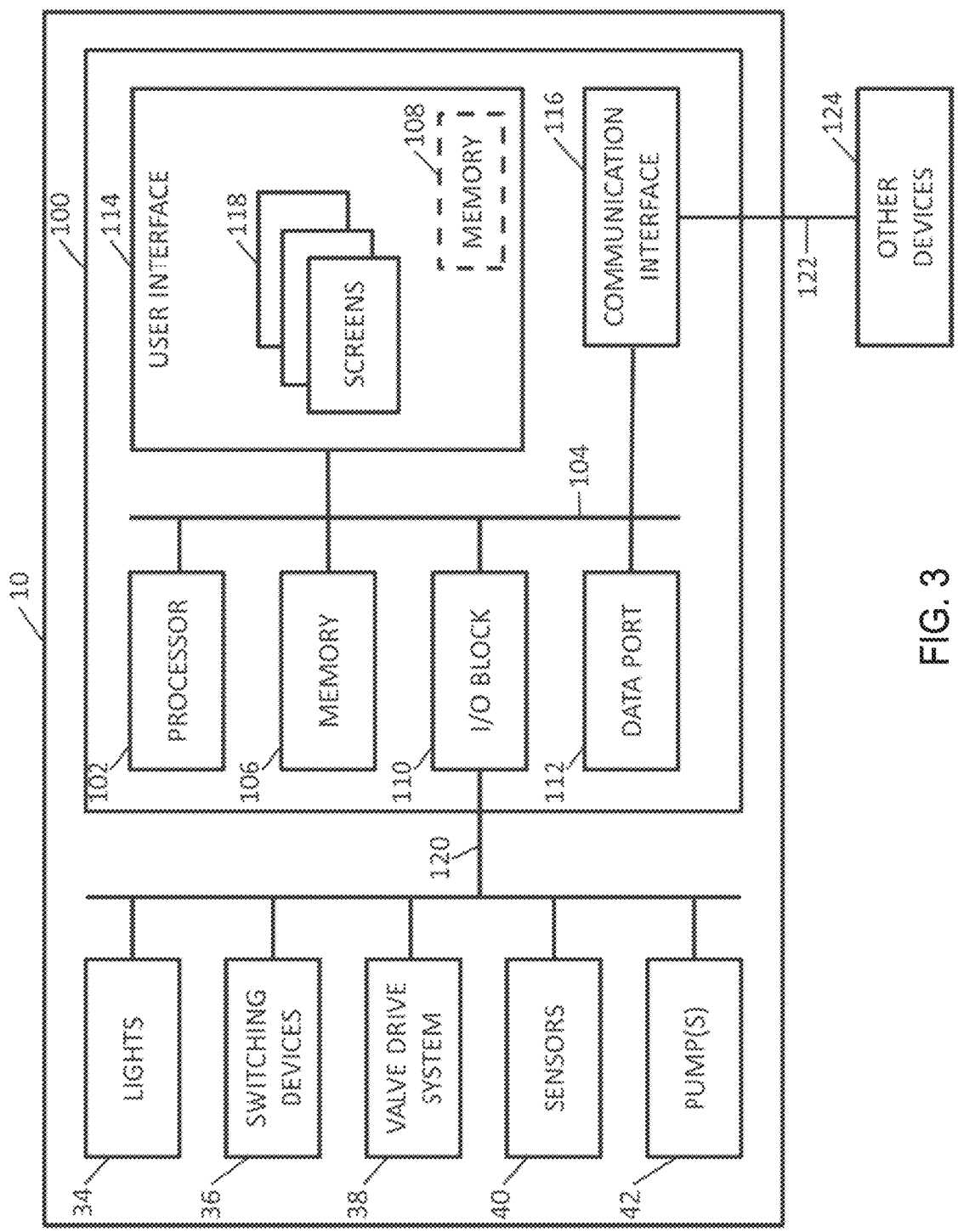
FIG. 3 is a schematic block diagram representation of an illustrative controller for a medical waste fluid collection cart.

FIG. 3 is a block diagram representation of an illustrative controller 100 for the medical waste fluid collection cart 10 of FIG. 1. In some cases, the medical waste fluid collection cart 10 may include one or more components capable of processing instructions for controlling one or more functions of the medical waste fluid collection cart 10. In some cases, the controller 100 may be included within the user interface 28 of FIG. 1. Alternatively, or in addition, one or more components of the controller 100 may be provided and/or mounted on the medical waste fluid collection cart 10 separate from the user interface 28. The controller 100 may include a processor 102 (e.g. microprocessor, microcontroller, etc.) that may be communicatively coupled via a data bus 104 to one or more components of the controller 100 including one or more units of memory 106, 108 (or memory located remote from the controller 100), an input/output block 110, a data port 112, a user interface 114, and/or a communication interface 116. In some cases, the user interface 114 may be configured to display one or more screens 118 to a user.

The processor 102 may operate using a control algorithm that controls or at least partially controls the collection of medical waste fluid and/or disposal of the collected medical waste fluid. The processor 102 may, for example, operate in accordance with an algorithm for collecting medical waste fluid from a surgical site during a medical procedure using one or more vacuum levels and/or fluid flow rates that may be specified by a user in real time and/or preset in the memory 106, 108, or other memory, for example.

In one example, the processor 102 may be configured to operate the algorithm(s) using an operating system (e.g., Windows, OS X, iOS, Android, Linux, Unix, GNU, etc.), or an example embedded operating system (e.g., QNX, NiagaraAX, Windows CE, etc.). In some cases, the controller 100 may include a timer (not shown). The timer may be integral to the processor 102 or may be provided as a separate component.

The memory 106, 108 of the illustrative controller 100 may be communicatively coupled to the processor 102. The memory 106, 108 may be used to store any desired information, such as the aforementioned control algorithm, a power monitoring algorithm, the configuration of the medical waste fluid collection and disposal system, set points, vacuum levels, flow levels, flags, indicators, diagnostic limits, look-up tables, sensed parameter correlations, and/or the like. The memory 106, 108 may be any suitable type of storage device including, but not limited to, RAM, ROM, EPROM, flash memory, a hard drive, and/or the like. In some cases, the processor 102 may store information within memory 106, 108, and may subsequently retrieve the stored information.

In some cases, the controller 100 may include an input/output block (I/O block) 110 for receiving one or more signals from one or more components of the medical waste fluid collection cart 10 and/or for providing one or more signals to the one or more components of the medical waste fluid collection cart 10. For example, the I/O block 110 may be configured to provide signals to and/or to receive signals from one or more lights 34 (e.g., container lights associated with the containers 18), one or more switching devices 36 (e.g., solenoids, relays, transistors, etc.), one or more components of a valve drive system 38 (e.g., motors, valves, etc.) including one or more components of the "wash" valve, the "drain" valve and/or the "vent" valve, one or more sensors 40 (e.g., light sensors, pressure sensors, level sensors, flow sensors, etc.), pumps 42 (e.g., a vacuum pump, an evacuation pump, etc.), and/or one or more other components via one or more communication paths 120. The VO block 110 may be configured for wired communication via one or more terminal screws, for example, and/or wireless communication via a wireless communication interface, for example. In some cases, the I/O block 110 may be used to communicate with other sensors and/or other devices associated with a particular medical process.

In some cases, as illustrated in FIG. 3, the controller 100 may include a data port 112. The data port 112 may be a wireless port for wireless protocols such as Bluetooth™, WiFi, Zigbee, or any other wireless protocol. In other cases, data port 112 may be a wired port such as a serial port, an ARCNET port, a parallel port, a CAT5 port, a USB (universal serial bus) port, and/or the like. In some cases, the data port 112 may use one or more communication protocols, such as Ethernet, BACNet, LONtalk, etc., that may be used via a wired network or a wireless network. In some instances, the data port 112 may be a USB port and may be used to download and/or upload information from a USB flash drive or some other data source. Other remote devices may also be employed, as desired.

The data port 112 may be configured to communicate with the processor 102 and may, if desired, be used to upload information to the processor 102 and/or download information from the processor 102. Information that can be uploaded and/or downloaded may include, for example, values of operating parameters (e.g., vacuum levels, flow rates, volume levels, fluid concentration levels, etc.), measurement correlations, look-up tables, and/or algorithms. In some instances, the data port 112 may be used to upload previously-created configurations and/or software updates into the controller 100 to hasten the programming process.

In some cases, the data port 112 may be used to download data stored within the memory 106, 108 for analysis and/or transfer to another device. For example, the data port 112 may be used to download one or more stored flow rates and/or vacuum levels, faults and/or alerts log, sensed data, and/or calculations based on sensed data to a remote device such as a USB memory stick (also sometimes referred to as a thumb drive or jump drive), personal computer, laptop, iPAD® or other tablet computer, PDA, smart phone, or other device, as desired. In some cases, the data may be convertible to an MS EXCEL®, MS WORD®, text, XML, and/or Adobe PDF® file, if desired.

In the illustrative embodiment of FIG. 3, the user interface 114 may be any suitable user interface that permits the controller 100 to display and/or solicit information, as well as accept one or more user interactions with the controller 100. For example, the user interface 114 may permit a user to enter data such as vacuum levels, patient information, start/end times of procedures, flow rates, medical application types, and the like. In some cases, the user interface 114 may include a display and a distinct keypad. A display may be any suitable display. In some instances, the display may include or may be a liquid crystal display (LCD), and in some cases a fixed segment display or a dot matrix LCD display. If desired, the user interface 114 may be a touch screen LCD panel that functions as both display and keypad. In some instances, a touch screen LCD panel may be adapted to solicit values for a number of operating parameters and/or to receive such values, if desired. In some cases, the user interface 114 may optionally include the memory 108. In some cases, the user interface 114 may include one or more electromechanical input devices (e.g., a switch, a potentiometer, a rotary dial, a push button, etc.) for use in selecting a desired flow rate, vacuum level, and/or parameter.

In one example, the user interface 114 may include a graphical user interface communicatively coupled to the processor 102 and/or the memory 106, 108 via the data bus 104. The user interface 114 may be configured to allow a user to monitor and/or control one or more functions of the medical waste fluid collection cart 10 and/or the evacuation station. The user interface 114 may include one or more screens 118 that may be used to present information to a user. In some cases, a graphical user interface may be used to solicit entry of vacuum levels, flow rates and/or other information from a user via a touchscreen, a keypad, buttons on the medical waste fluid collection cart 10, and/or another electromechanical input device (e.g., a dial interface).

The communication interface 116 may include one or more communication interfaces for allowing the controller 100 to communicate with one or more other devices 124, such as via a communication link 122. For example, the communication interface 116 may include a communication interface that allows the medical waste fluid collection cart 10 to communicate with the evacuation station via the coupler 30. In some cases, one or more connectors associated with the communication link 122 may be included within the coupler 30. In other cases, the communication link 122 may be separate from the coupler 30. In some cases, the communication interface 116 may include one or more wired and/or wireless communication interfaces, such as an Ethernet port, a wireless port, an RS-232 port, an RS-422 port, an RS-485 port, and the like. In such cases, the communication interface 116 may allow data entry, reprogramming, upgrading, debugging, and/or other operations to be done remotely, such as by an authorized user, via the communication link 122.

Figure 4:
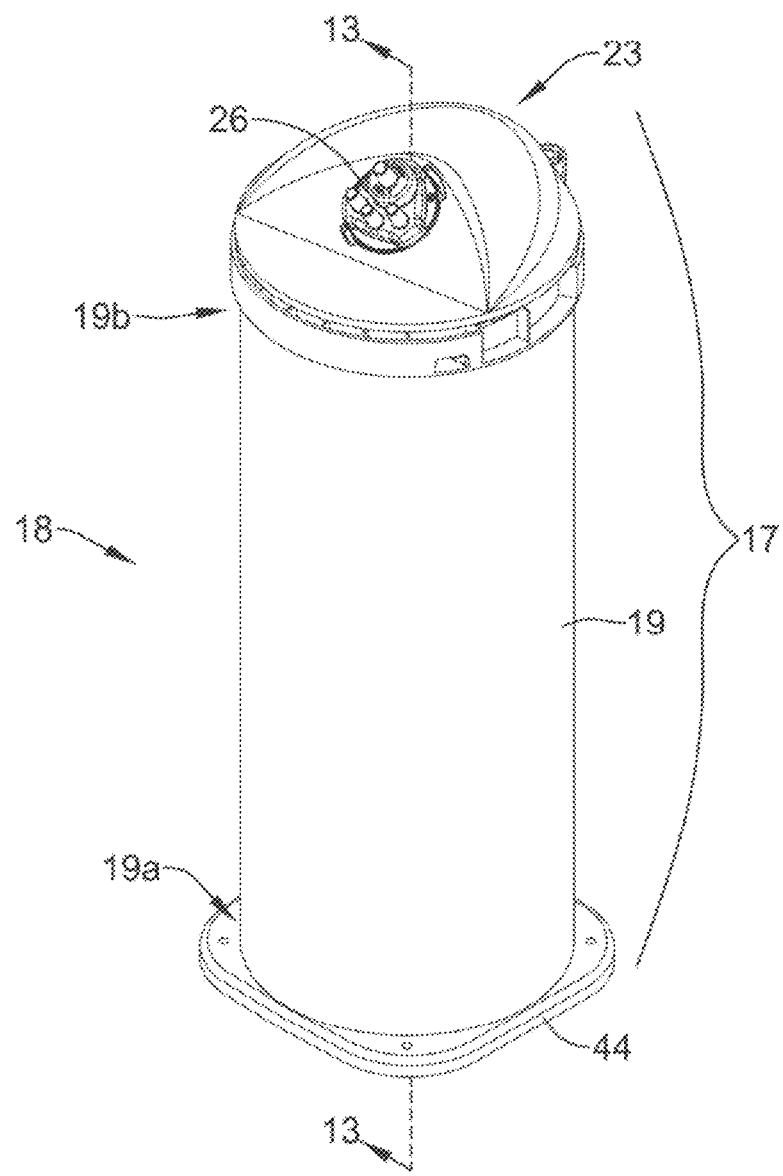
FIG. 4 is a perspective view of a fluid waste container assembly.

FIG. 4 is an illustrative container assembly 17 including a container 18, a lid assembly 23, and a base 44. The container 18 may have a body 19 with a bottom 19a and a top 19b, where the base 44 may be located adjacent the bottom 19a of the body 19 and the lid assembly 23 may be located adjacent the top 19b of the body 19.

Figure 5:
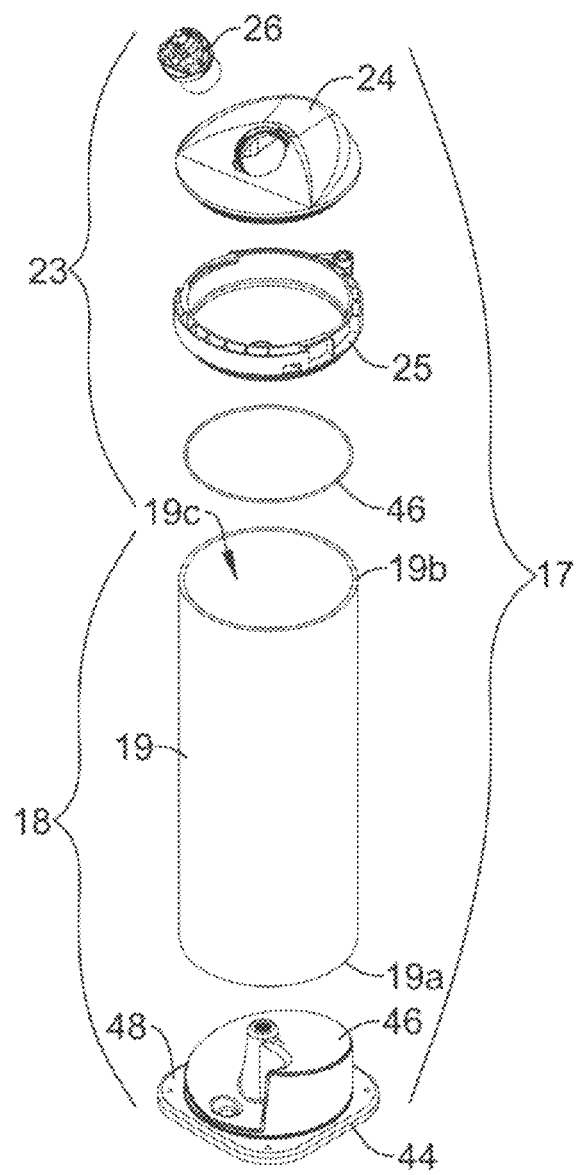
FIG. 5 is an exploded perspective view of a fluid waste container assembly.

FIG. 5 is an exploded view of the container assembly 17. As shown in FIG. 5, the lid assembly 23 may include a lid 24 and a lid ring 25. Illustratively, the lid ring 25 may engage the top 19b of the body 19 and the lid 24 may engage the lid ring 25 to close at least a portion of an opening into the container 18 and provide selective access to an interior of the container 18.

The container 18 may be any shape and size configured to fit at least partially within the housing 12 of the fluid waste collection cart 10, or otherwise be positioned on the cart 10. As shown in FIG. 5, the body 19 of the container 18 may be a cylinder shape (e.g., a shape with a rounded or circular cross-section) with at least partially open ends (e.g., the bottom 19a and the top 19b) and a lumen 19c extending between each end. Alternatively, or in addition, the body 19 of the container 18 may have a cross-sectional shape different than a circle, such as a square, rectangle, oval, or other two-dimensional shape. In some cases, the bottom 19a of the body 19 may include a base (e.g., base 44 or other base) separately connected with, integrally connected to, or monolithically formed with the body 19 of the container 18. When the base 44 is connected to the body 19, the base 44 may be connected to the body 19 with any connection technique, including, but not limited to, an adhesive connection, a force fit connection, a threaded connection, a bayonet connection, a twist lock connection, and/or one or more other permanent or reversible connection technique.

In some instances, the lid assembly 23 may include an o-ring 45. The o-ring 45 may engage the lid ring 25 and create a liquid tight seal between the lid ring 25 and the container 18 (e.g., the body 19) when the lid ring 25 is engaging the container 18. The o-ring 45 may be configured to facilitate or further a friction fit connection, a threaded connection, a bayonet connection, a twist lock connection, and/or one or more other connection types between the lid ring 25 and the container 18.

The lid assembly may include a manifold 26. The manifold 26 may be configured to releasably connect to the lid 24. In some cases, the manifold 26 may be configured to be removed from the lid 24 after use and may be disposable. The manifold 26 may include one or more ports for providing access to the containers 18. In one example, the one or more ports may be configured to connect to tubing and may include one or more suction ports for connecting to a suction tube, one or more vacuum ports for connecting to a vacuum tube, and/or one or more other ports.

The manifold 26 may be configured to engage the lid 24 in one or more manners. The manifold 26 may connect to or engage the lid 24 through a threaded connection, a force fit connection, a bayonet connection, twist lock connection, and/or one or more other connection types. In some cases, an air-tight or hermetic seal may be formed between the manifold 26 and the lid 24.

The base 44 may include a top portion 46 and a bottom portion 48. In one example, at least part of the top portion 46 may be sized and configured to fit through the bottom 19a of the body 19 of the container 18 and within the lumen 19c of the body 19. The bottom 19a of the body 19 may rest on the bottom portion 48 of the base 44 and/or extend on the side(s) of the bottom portion 48. An air-tight or hermetic seal may be formed between the body 19 of the container 18 and the base 44.

Figure 6:
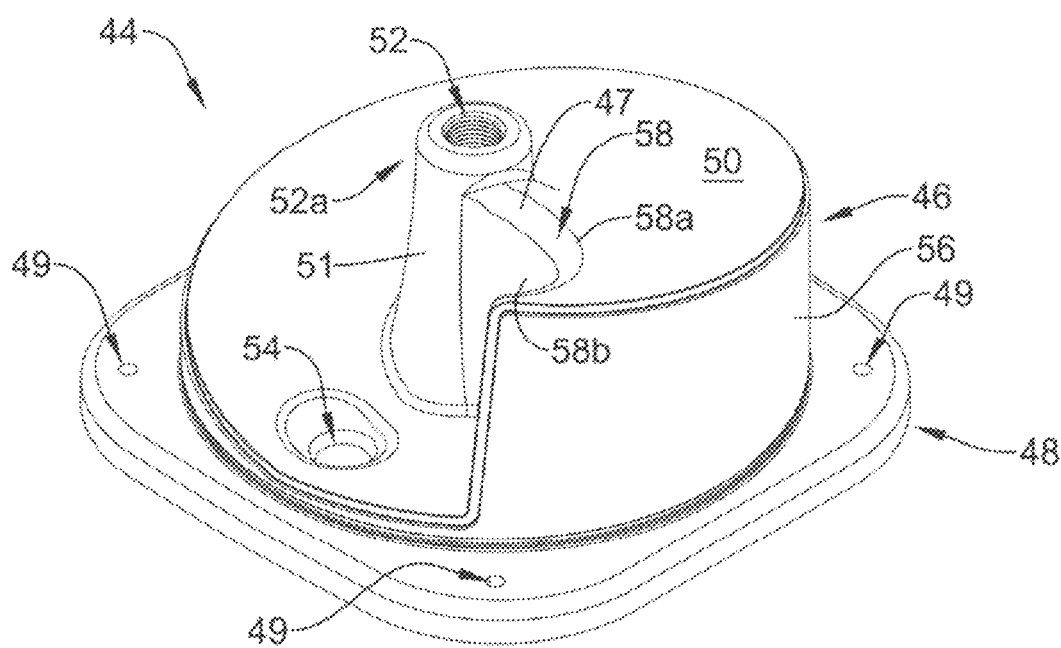
FIG. 6 is a perspective view of a base of a fluid waste container assembly.

FIG. 6 is a top perspective view of the base 44. As shown in FIG. 6, the base 44 may include a top portion 46 and a bottom portion 48, wherein the bottom portion 48 may have a footprint width (F2 in FIG. 11) at least as wide as or wider than a footprint width (F1 in FIG. 11) of the top portion 46. Alternatively, or in addition, at least a portion of a footprint width of the top portion 46 may be wider than a footprint width of the bottom portion 48 The top portion 46 and the bottom portion 48 may be monolithically formed or two or more pieces integrally joined together. In some cases, the bottom portion 48 may have one or more holes 49 for receiving a fastener to fasten the container 18 to the cart 10.

The top portion 46 of the base 44 may have an interior surface 50, a spray hole or opening 52, a drain hole or opening 54, and a perimeter wall 56 that may extend from the bottom portion 48 and may have a top that at least partially defines an outer perimeter of the interior surface 50 and/or an outer perimeter of the top portion 46. The spray opening 52 may allow for injecting cleaning fluids and other fluids into the container 18 before, during, and/or after use of the container 18. The drain opening 54 may be configured to facilitate removal of solid (bone chips, clots, etc.) and fluid waste from the container 18 through a drain and/or hose connected to the drain opening.

The spray opening 52 may be at least partially defined by an extension 51 (e.g., a post or other feature) extending from or through the base 44 into an interior of the container 18, and the spray opening 52 may extend from a first end 52a to a second end 52b through the extension 51. The first end 52a of the spray opening 52 may be located within the container 18 when the base is enclosing an end of the body 19. The first end 52a may include or may be configured to receive a spray nozzle 53 (see FIG. 13), where cleaning fluids or other fluids may pass through the spray opening 52 and out a top portion of the spray nozzle 53 positioned within the interior of the container 18. In some cases, the spray nozzle 53 may connect to the first end 52a through one or more of a threaded connection, a friction fit connection, a bayonet connection, a twist lock connection, an adhesive connection, and/or one or more other connections. The second end 52b of the spray opening 52 may be configured to connect to a hose for passing fluids (e.g., cleaning fluids or other fluids) to the spray opening 52.

The base 44 may include a radial ledge 47 and/or a radial wall 58 that extends from the spray opening 52 and/or a central portion of the base 44 toward and/or to the perimeter wall 56. The radial ledge 47 and/or the radial wall 58 may extend radially in a substantially linear manner or in a non-linear (e.g., a curved, a stepped, etc.) manner. In one example, as shown in FIG. 6, the radial wall 58 may extend radially in a curved manner. The radial ledge 47 may be rounded and/or may be formed by two or more surfaces coming together.

As shown in FIG. 6, the interior surface 50 of the base 44 may extend in or along a path from a first side 58a (e.g., a convex side, as shown in FIG. 6) of the radial wall 58 of the base 44 toward the drain opening 54 and a second side 58b (e.g., a concave side, as shown in FIG. 6) of the radial wall 58 opposite the first side 58a. The interior surface 50 may extend to a location adjacent the drain opening 54, a location adjacent the second side 58b of the radial wall 58 and/or extend under the radial ledge 47. The path of the interior surface 50 may be helical, one example of which is shown in the Figures. The helical path along which the interior surface 50 may extend may be a path that is coiled, ramped, spiraled, and/or configured in another manner that at least partially declines around a point of rotation from a starting point to an end point adjacent the drain opening 54. Although the interior surface 50 in the Figures extends along a helical path that follows a cylindrical perimeter, the interior surface 50 may extend along a helical path that follows a perimeter of a shape other than a cylinder (e.g., a cuboid, a cube, a prism, a pyramid, an ovoid, etc.).

In some cases, the path of the interior surface 50 may extend around the extension 51, around the spray opening 52, and/or around a central portion of the base 44. In instances when the path of the interior surface 50 extends around the extension 51 and/or the spray opening 52, the interior surface 50 may be entirely below the first end 52a of the spray opening 52, the interior surface 50 may start at a level of the first end 52a and extend below the first end 52a, the interior surface 50 may be at least partially above and at least partially below the first end 52a, the interior surface 50 may extend from above the first end 52a to a level of the first end 52a, or the interior surface 50 may be entirely above the first end 52a. The central portion of the base 44 may be considered a portion of the base 44 spaced from the perimeter wall 56 and positioned toward a central axis of the container 18 extending through the base 44 when the base 44 is enclosing an end of the body 19 of the container 18. In some instances, the central portion of the base 44 need not be centered within the container 18. In some instances, the longitudinal axis of the extension 51 may be centered within the container 18, while in other instances, the longitudinal axis of the extension 51 may be offset from the center of the container 18.

The interior surface 50 may angle or decline toward the drain opening 54. For example, the interior surface 50 may decline along the helical path from an upper most point adjacent the first side 58a of the radial wall 58 to a location adjacent the drain opening 54 and/or the second side 58b of the radial wall 58. In some cases, the decline of the interior surface 50 may end at or adjacent the drain opening 54. In such cases, the interior surface 50 extending between the second side 58b of the radial wall 58 and the drain opening 54 may be horizontal or angled at a decline toward the drain opening 54 (see FIG. 7).

The decline(s) of the interior surface 50 may be continuous or discontinuous. For example, as in FIG. 6, the decline of the interior surface 50 may be continuous. Alternatively, the interior surface 50 may be separated into steps or other discontinuous features having runs that are flat or angled in a declining manner along the helical path. In some cases, the angle at which the interior surface 50 declines may be consistent along the helical path. Alternatively, the angle at which the interior surface 50 declines may increase or decrease along the helical path.

Figure 7:
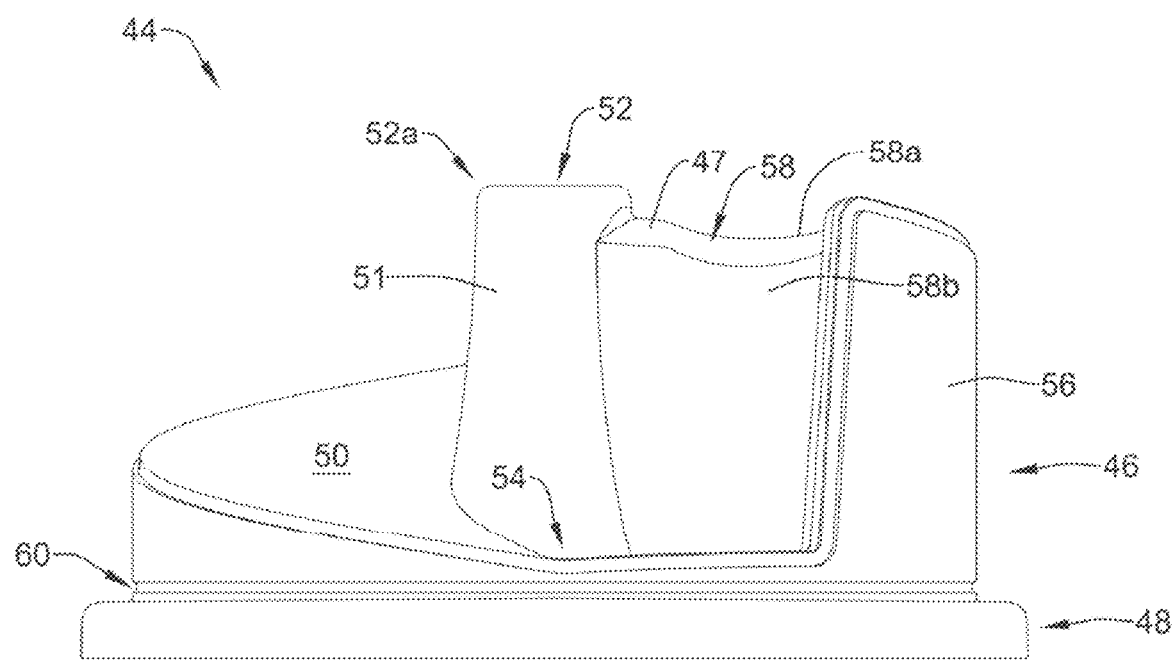
FIG. 7 is a side view of the base of a fluid waste container assembly shown in FIG. 6.
Figure 13:
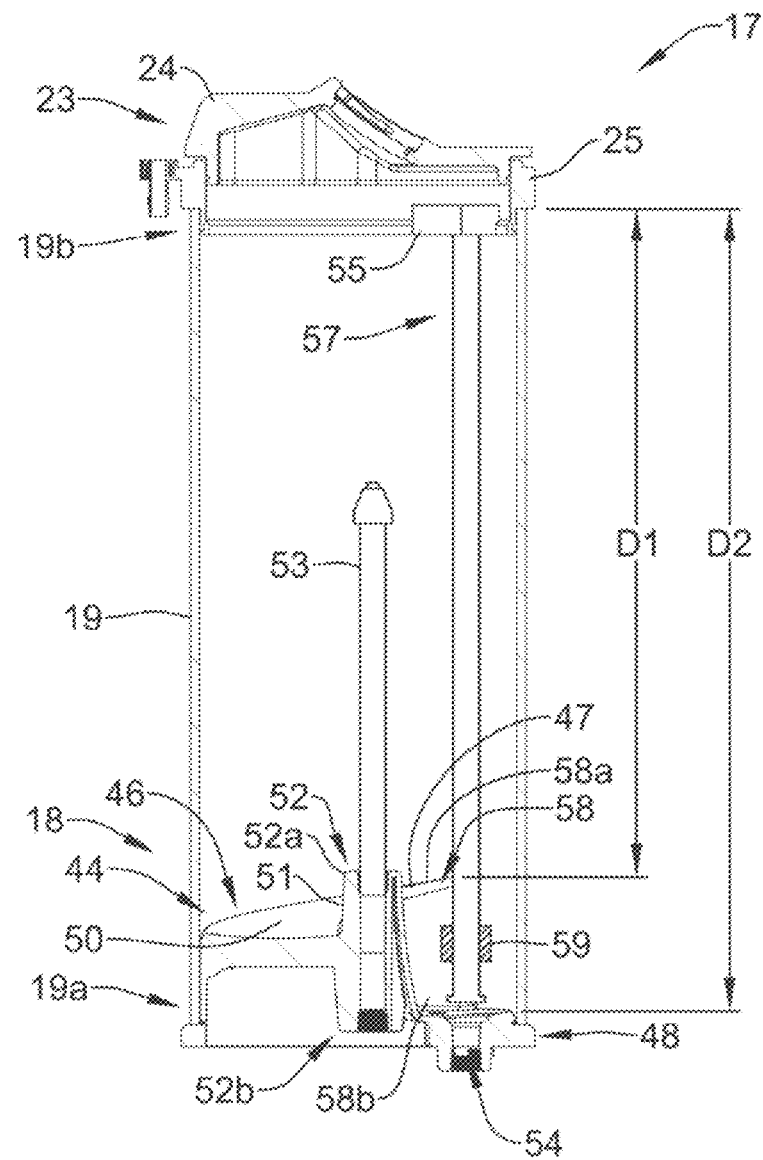
FIG. 13 is a cross-sectional view of the fluid waste container assembly in FIG. 4, taken along line 13-13.

FIG. 7 is a side view of the base 44 showing the helical path of the interior surface 50 terminating adjacent the second side 58b of the radial wall 58. In FIG. 7, the decline of the interior surface 50 along the helical path declines toward a location at or adjacent the drain opening 54. Additionally, the interior surface 50 is depicted in FIG. 7 as declining from the second side 58b of the radial wall toward a location adjacent the drain opening 54. Such a decline(s) of the interior surface 50 may facilitate directing solids into the drain opening 54 and away from a level sensor 57 (e.g., away from a float 59 of the level sensor 57, as shown in FIG. 13, positioned adjacent to and movable along the radial wall 58, to prevent solids (e.g., clogs or build-ups of solids) and from interfering with the level sensor 57 and facilitate draining solids and liquids through the drain opening 54) from being positioned adjacent the radial wall 58 and facilitate draining collected fluid waste, as discussed further below.

The base 44 may include an indent 60 configured to receive an o-ring (not shown). When the base 44 connects with the body 19 of the container 18, the indent 60 and an associated o-ring may facilitate creating a hermetic seal between the base 44 and the body 19.

Figure 8:
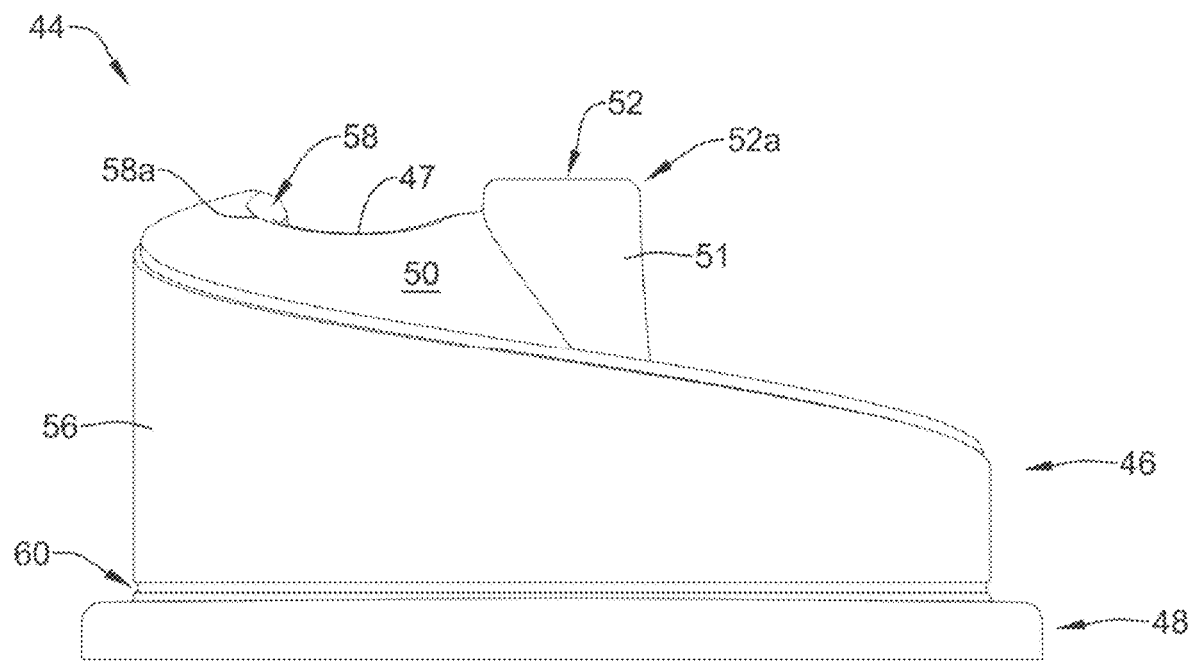
FIG. 8 is a side view of the base of a fluid waste container assembly shown in FIG. 6.

FIG. 8 is a side view of the base 44 opposite the side view depicted in FIG. 7. FIG. 8 shows the interior surface 50 declining along the helical path from a location adjacent the first side 58a of the radial wall 58.

Figure 9:
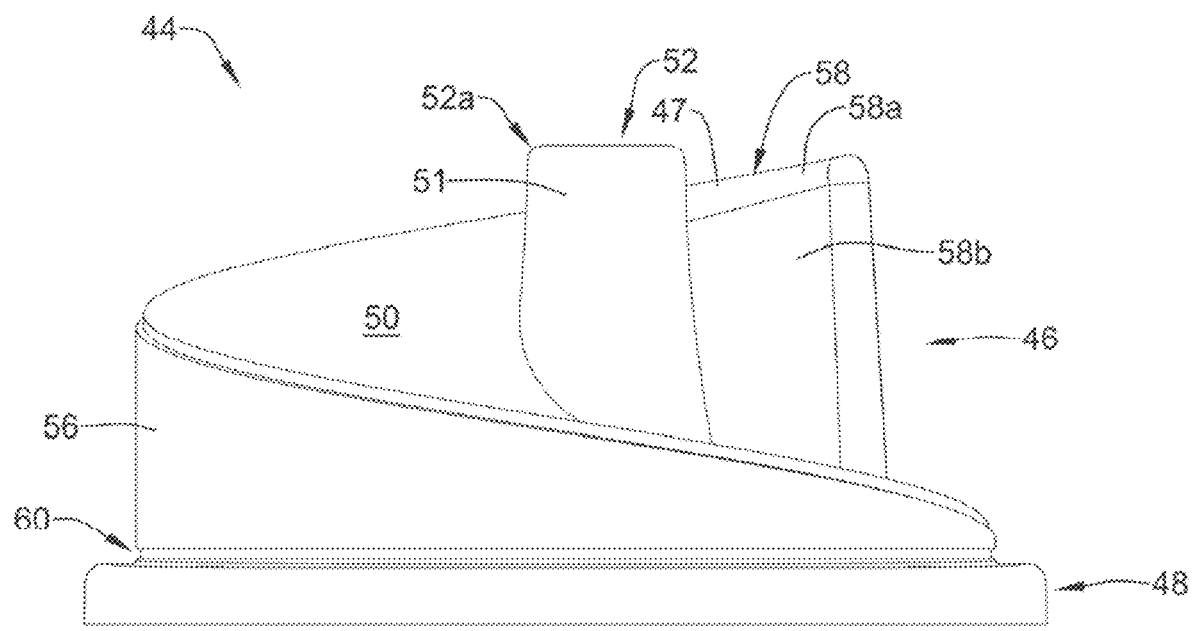
FIG. 9 is a side view of the base of a fluid waste container assembly shown in FIG. 6.

FIG. 9 is a side view of the base 44 rotated ninety (90) degrees from the side views depicted in FIGS. 7 and 8. FIG. 9 shows the interior surface 50 declining along the helical path from a location adjacent the first side 58a of the radial wall 58.

Figure 10:
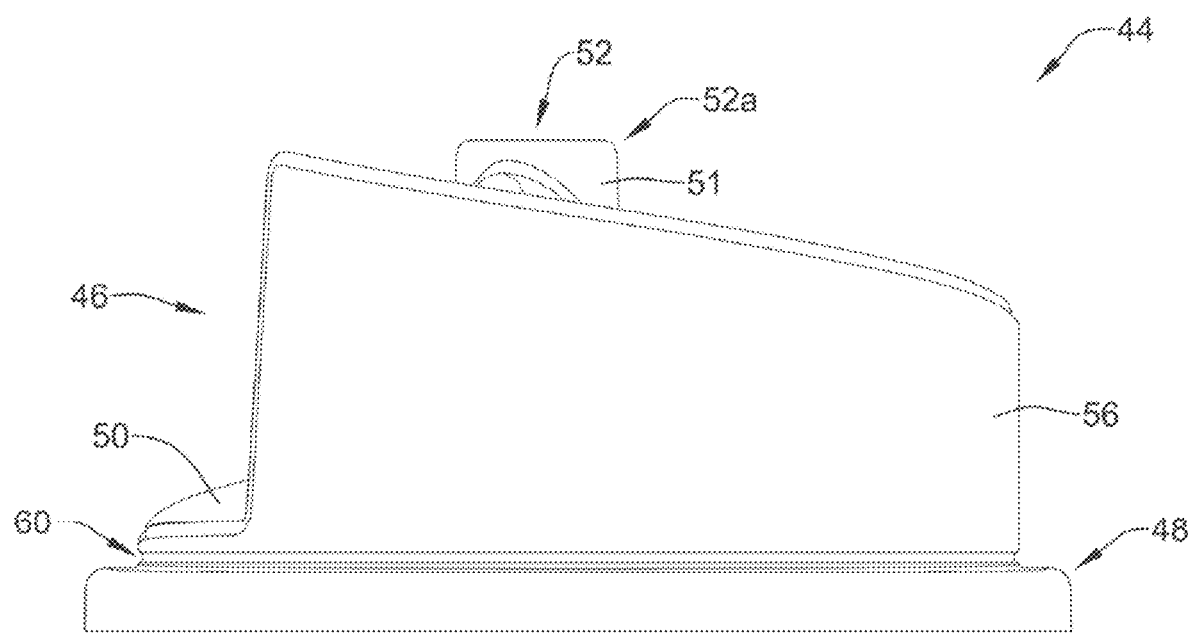
FIG. 10 is a side view of the base of a fluid waste container assembly shown in FIG. 6.

FIG. 10 is a side view of the base 44 opposite the side view depicted in FIG. 9. FIG. 10 shows the decline of the interior surface 50 along the helical path about the spray opening 52.

Figure 11:
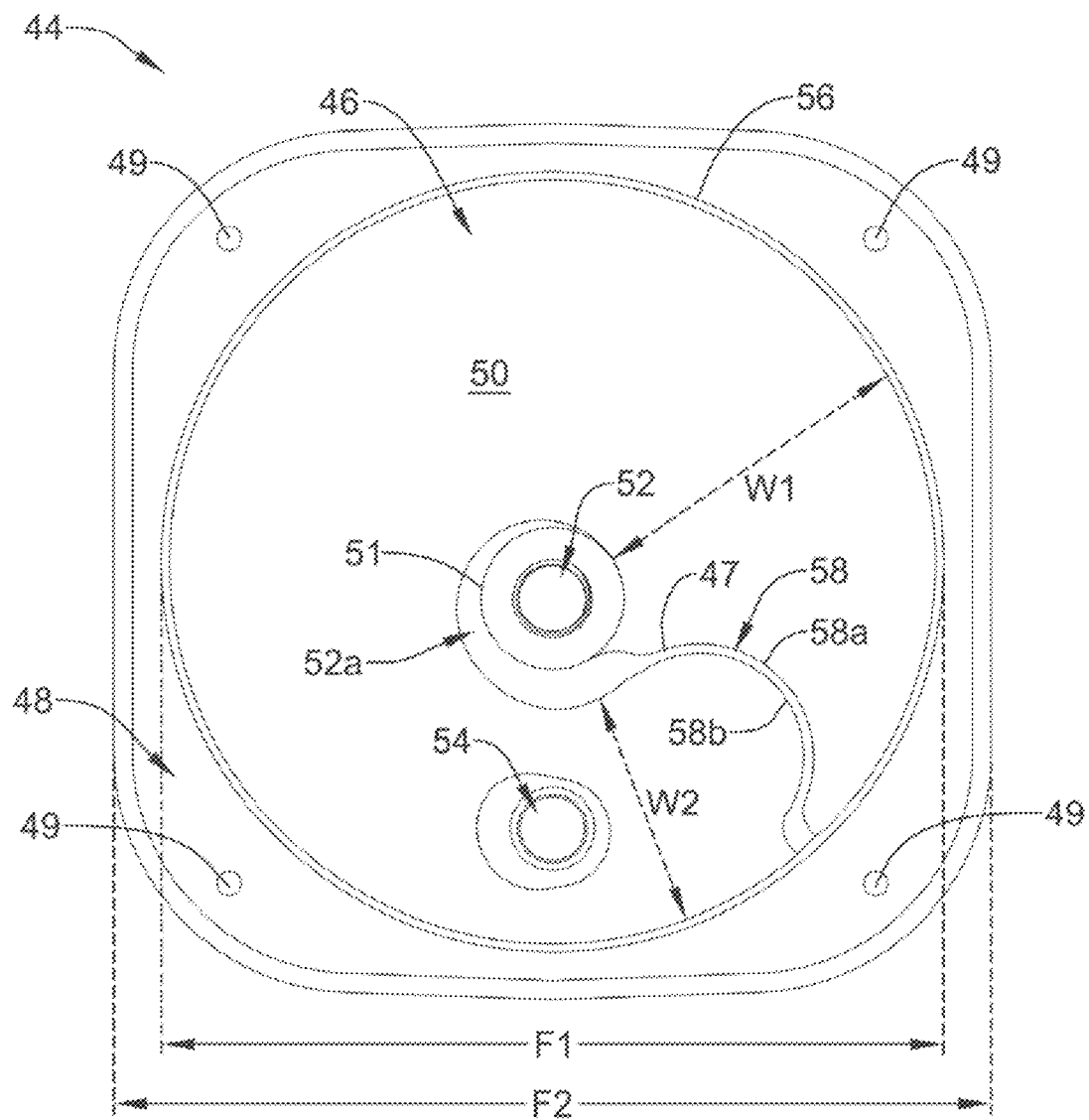
FIG. 11 is a top view of the base of a fluid waste container assembly shown in FIG. 6.

FIG. 11 is a top view of the base 44. The top view of FIG. 11 depicts the interior surface 50 extending along the helical path around the spray opening 52 from the first side 58a of the radial wall 58 to the second side 58b of the radial wall 58. In some instances, the width of the interior surface 50 may stay constant along the helical path. Alternatively, a width of the interior surface 50 may increase or decrease along the helical path. As shown in FIG. 11, the interior surface 50 tapers along the helical path as a width W1 adjacent the beginning of the helical path (i.e., portion furthest from the drain opening 54) is greater than a width W2 adjacent the ending of the helical path (i.e., portion closest to the drain opening 54). The interior surface 50 may taper to facilitate directing the solids in the fluid of the container 18 away from the body 19 of the container 18 and into a middle of the interior surface 50 as those solids are directed along the helical path toward the drain opening 54. The spray opening 52 may be offset from a central axis of the base 44 to facilitate a taper of the interior surface 50 and/or other purposes.

Figure 12:
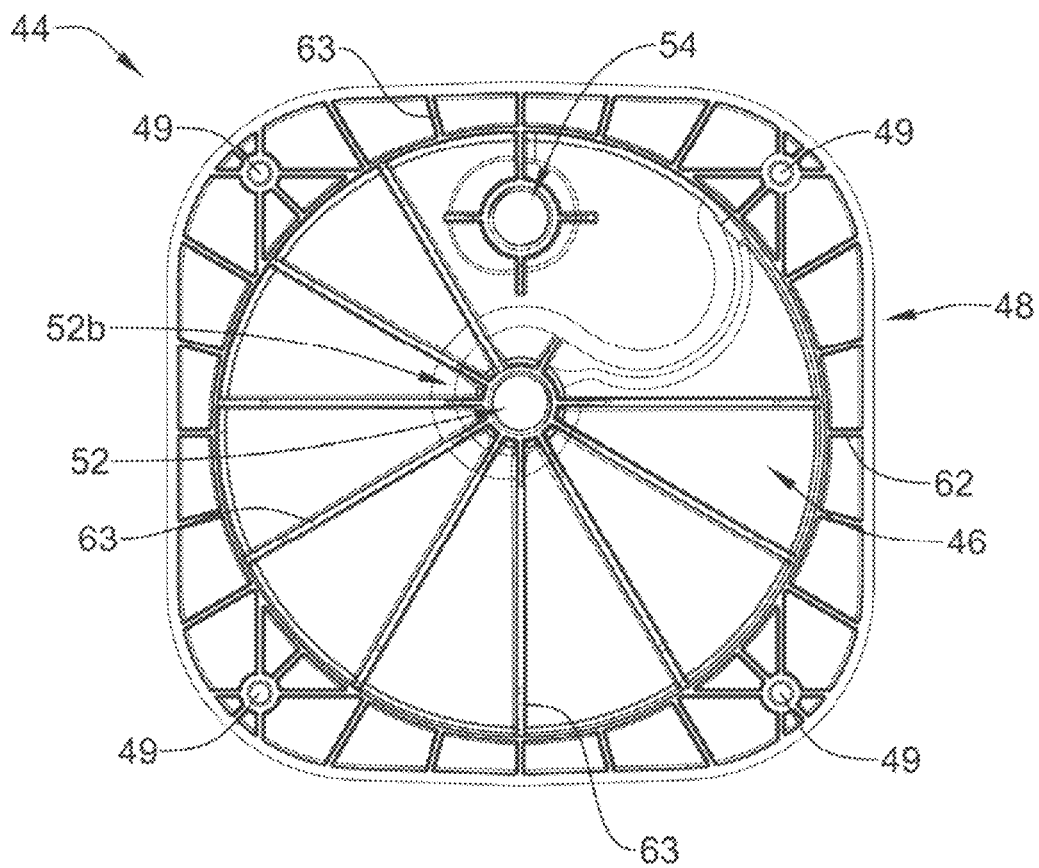
FIG. 12 is a bottom view of the base of a fluid waste container assembly shown in FIG. 6.

FIG. 12 is a bottom view of the base 44 opposite the top view depicted in FIG. 11. The spray opening 52, the drain opening 54, and the holes 49 configured to receive fasteners may extend through the base 44. One or more support features 63 (only a select few support features 63 are labeled FIG. 12 for clarity purposes) within the base 44 be provided to support the base 44 during manufacturing of the base 44 and during use of the base 44.

FIG. 13 is a cross-section of the container assembly 17 of FIG. 4 taken along line 13-13. FIG. 13 depicts the decline of the interior surface 50 along the helical path. For example, dotted line D1 represents a distance from the interior surface 50 at or adjacent a beginning of the helical path to a top rim of the body 19 and dotted line D2 represents a distance from the interior surface 50 at or adjacent an end of the helical path to the top rim of the body 19. Here, D1 is a distance that is less than a distance of D2.

A fluid level sensor 57 is depicted in FIG. 13. Although the fluid level sensor 57 may extend from one or more of the base 44, the lid assembly 23, and the body 19, the level sensor 57 shown in FIG. 13 extends from a holder 55 of lid ring 25 toward the base 44 adjacent the drain opening 54 and the radial wall 58.

The level sensor 57 may be any type of level sensor 57 capable of measuring an amount of material in the container 18. In FIG. 13, the level sensor 57 may include a float 59 configured to float along an elongated member 61 as the container fills up with or is drained of material. The level sensor 57 may provide a visual indication of the material level in the container 18 based on markings on or adjacent the level sensor 57 and a position of the float 59 along the elongated member 61. Alternatively, or in addition, the level sensor 57 may communicate with the controller 100 or other controller and a fluid level measurement may be displayed on a user interface 28 or other user interface.

Figure 14:
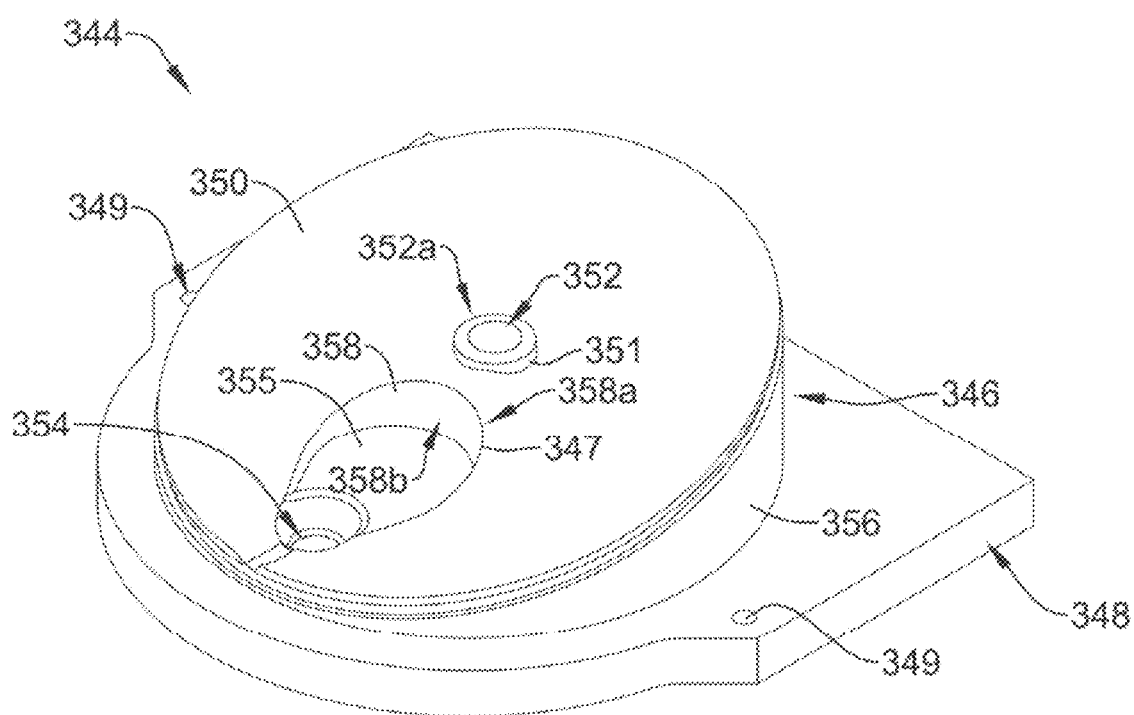
FIG. 14 is a perspective view of a base of a fluid waste container assembly.

FIG. 14 is a top perspective view of an alternative base (e.g., base 344) for container 18 of the container assembly 17. As shown in FIG. 14, the base 344 may include a top portion 346 and a bottom portion 348. The top portion 346 and the bottom portion 348 may be monolithically formed or may be two or more pieces integrally joined together. In some cases, the bottom portion 348 may have one or more holes 349 for receiving a fastener to fasten the container 18 to the cart 10.

The top portion 346 of the base 344 may have an interior surface 350, a spray hole or opening 352, a drain hole or opening 354, and a perimeter wall 356 that may extend from the bottom portion 348 and may have a top that at least partially defines an outer perimeter of the interior surface 350 and/or an outer perimeter of the top portion 346. The spray opening 352 may allow for injecting cleaning fluids and other fluids into the container 18 before, during, and/or after use of the container 18. The drain opening 354 may be configured to facilitate removal of solid (bone chips, clots, etc.) and fluid waste from the container 18 through a drain and/or hose connected to the drain opening 354.

The spray opening 352 may be at least partially defined by an extension 351 (e.g., a post or other feature) extending through and/or from the base 344 into the interior of the container 18 and may extend from a first end 352a to a second end 352b (see FIG. 20) through the extension 351. The first end 352a of the spray opening 352 may be located within the container 18 when the base 344 is enclosing an end of the body 19. The first end 352a may include or may be configured to receive a spray nozzle 53, where cleaning fluids or other fluids may pass through the spray opening 352 and out a top portion of the spray nozzle 53 positioned within the interior of the container 18. In some cases, the spray nozzle 53 may connect to the first end 352a through one or more of a threaded connection, a friction fit connection, a bayonet connection, a twist lock connection, an adhesive connection, and/or one or more other connections. The second end 352b of the spray opening 352 may be configured to connect to a hose for passing fluids (e.g., cleaning fluids or other fluids) to the spray opening 352.

The base 344 may include a ledge 347 and/or a wall 358, where the wall 358 may extend from the interior surface 350 to a base surface 355 (e.g., a surface from which a fluid level is measured). The ledge 347 and/or the wall 358 may form any shape. In one example, as shown in FIG. 14, the ledge 347 and the wall 358 may have a curved or rounded form and extend to and from a location adjacent the drain opening 354.

As shown in FIG. 14, the interior surface 350 of the base 344 may have an outer perimeter at least partially defined by the perimeter wall 356 and an inner perimeter at least partially defined by the ledge 347 or wall 358. The interior surface 350 may extend to a location adjacent the drain opening 354 and/or the base surface 355. The interior surface 350 may follow a path that directs collected medical waste toward the drain opening 354 and solids of the medical waste away from the base surface 355. The path may decline toward the drain hole and may take on any shape (e.g., a ramped crescent or circular shape, as shown in FIG. 14, or other shape).

In some cases, the path of the interior surface 350 may extend around the extension 351, around the spray opening 352, and/or around a central portion of the base 344. In instances when the path of the interior surface 350 extends around the extension 351 and/or the spray opening 352, the interior surface 350 may be entirely below the first end 352a of the spray opening 352, the interior surface 350 may start at a level of the first end 352a and extend below the first end 352a, the interior surface 350 may be at least partially above and at least partially below the first end 352a, the interior surface 350 may extend from above the first end 352a to a level of the first end 352a, or the interior surface 350 be entirely above the first end 352a. The central portion of the base 344 may be considered a portion of the base 344 spaced from the perimeter wall 356 and adjacent a central axis of the container 18 extending through the base 344 when the base 344 is enclosing an end of the body 19 of the container 18. The extension 351 of the central portion of the base 344 need not be centered within the container 18. For example, in some instances the longitudinal axis of the extension 351 may be centered in the base 344, while in other instances the longitudinal axis of the extension 351 may be offset from the center of the base 344.

As mentioned, the interior surface 350 may decline toward the drain opening 354 and the decline(s) of the interior surface 350 may be continuous or discontinuous. For example, as in FIG. 14, the decline of the interior surface 350 may be continuous. Alternatively, the interior surface 350 may be separated into steps or other discontinuous features having runs that are flat or angled in a declining manner along the path of the interior surface 350. In some cases, the angle at which the interior surface 350 declines may be consistent along the path toward the drain opening 354. Alternatively, the angle at which the interior surface 350 declines may increase or decrease along the path toward the drain opening 354.

Figure 15:
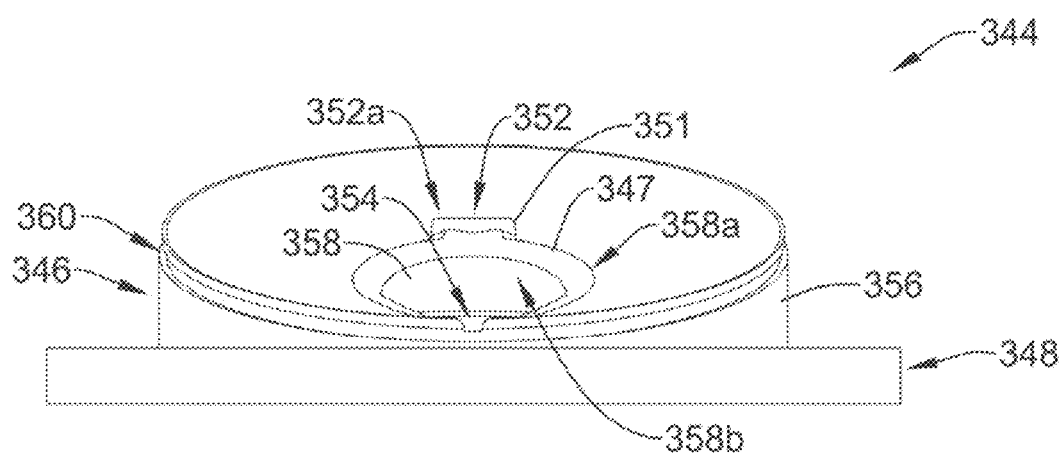
FIG. 15 is a side view of the base of a fluid waste container assembly shown in FIG. 14.

FIG. 15 is a side view of the base 344 showing the path of the interior surface 350 declining and terminating adjacent drain opening 354 at a first side and at a second side of the drain opening 354. Such a decline(s) of the interior surface 350 may facilitate directing solids into the drain opening 354 and away from the base surface 355 and the level sensor 57 (e.g., away from the float 59 of the level sensor 57, as shown in FIG. 13, to prevent solids (e.g., clogs or build-ups of solids) from interfering with the level sensor 57 and facilitate draining solids and liquids through the drain opening 354) positionable adjacent the wall 358.

The base 344 may include an indent 360 configured to receive an o-ring (not shown). When the base 344 connects with the body 19 of the container 18, the indent 360 and an associated o-ring may facilitate creating a hermetic seal between the base 344 and the body 19.

Figure 16:
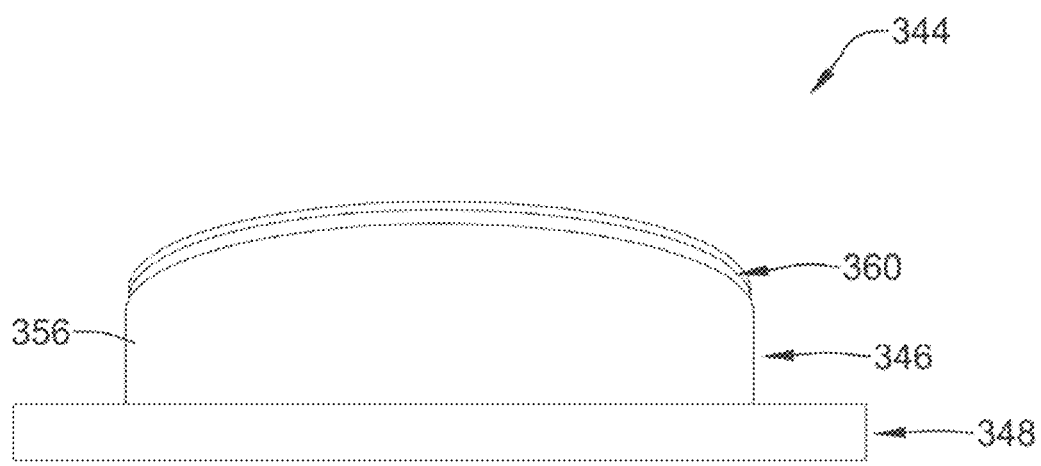
FIG. 16 is a side view of the base of a fluid waste container assembly shown in FIG. 14.

FIG. 16 is a side view of the base 344 opposite the side view depicted in FIG. 15. FIG. 16 shows the top portion 346 and the bottom portion 348, with the indent 360 formed in the top portion 346. As shown in FIG. 16, the perimeter wall 356 of the top portion 346 may decline toward an opposite side of the base 344.

Figure 17:
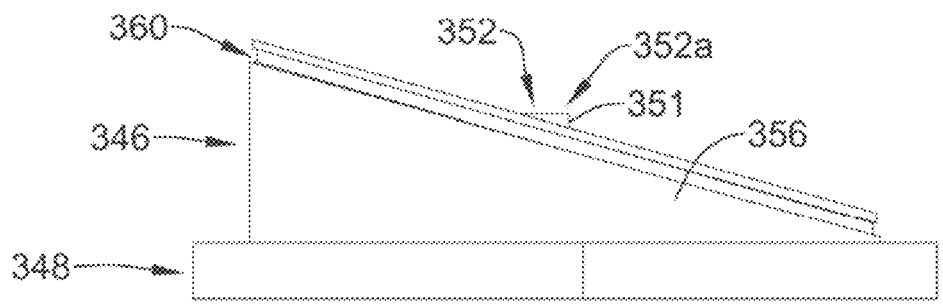
FIG. 17 is a side view of the base of a fluid waste container assembly shown in FIG. 14.

FIG. 17 is a side view of the base 44 rotated ninety (90) degrees from the side views depicted in FIGS. 15 and 16. FIG. 17 shows the perimeter wall 356 of the base 344 declining along a width of the top portion 346 of the base 344.

Figure 18:
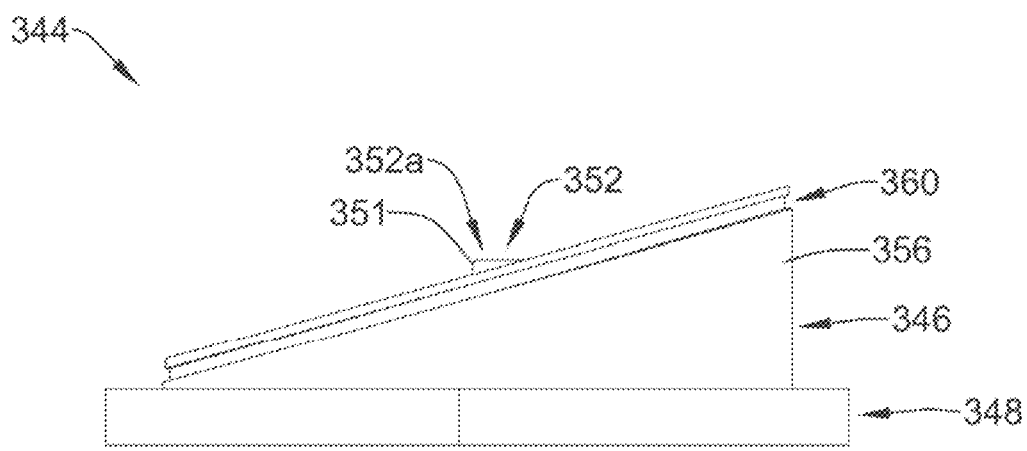
FIG. 18 is a side view of the base of a fluid waste container assembly shown in FIG. 14.

FIG. 18 is a side view of the base 344 opposite the side view depicted in FIG. 17. FIG. 18 shows the decline of the perimeter wall 356 of the base 344 along a width of the top portion 346 of the base 344.

Figure 19:
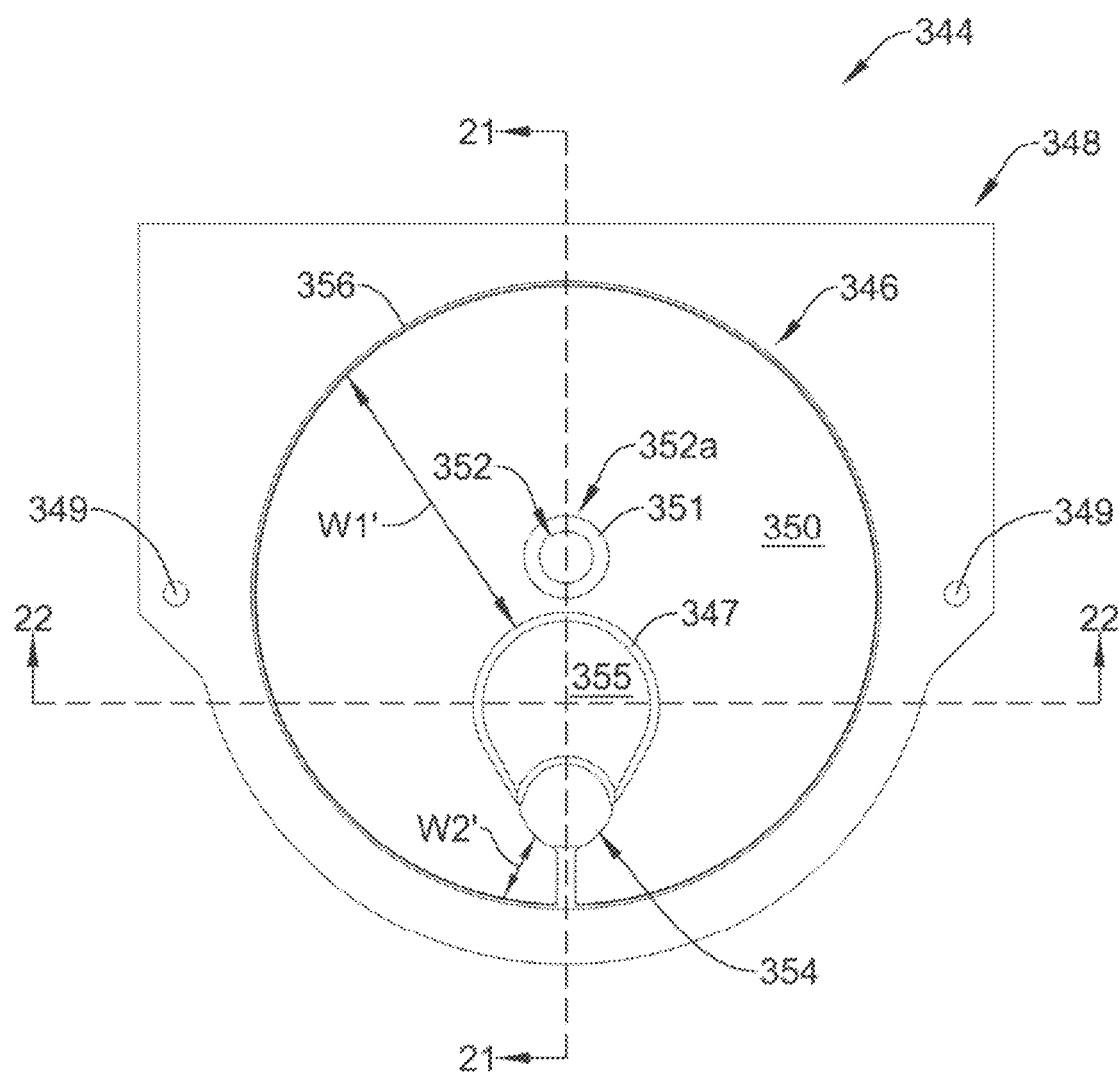
FIG. 19 is a top view of the base of a fluid waste container assembly shown in FIG. 14.

FIG. 19 is a top view of the base 344. The top view of FIG. 19 depicts the interior surface 350 extending along the path around the spray opening 352 and around the base surface 355 between a top of the perimeter wall 356 and the ledge 347. In some instances, the width of the interior surface 50 may stay constant along the path toward the drain opening 354. Alternatively, a width of the interior surface 350 may increase or decrease along the path. As shown in FIG. 19, the interior surface 350 may taper along the path as a width W1' adjacent the beginning of the path (e.g., portion furthest from the drain opening 354) is greater than a width W2' adjacent the ending of the path (e.g., portion closest to the drain opening 354). The interior surface 350 may taper to facilitate directing the solids in the fluid of the container 18 away from the body 19 of the container 18 and into a middle of the interior surface 350 as those solids are directed along the path toward the drain opening 354. The spray opening 352 may be at or offset from a central axis of the base 344.

Figure 20:
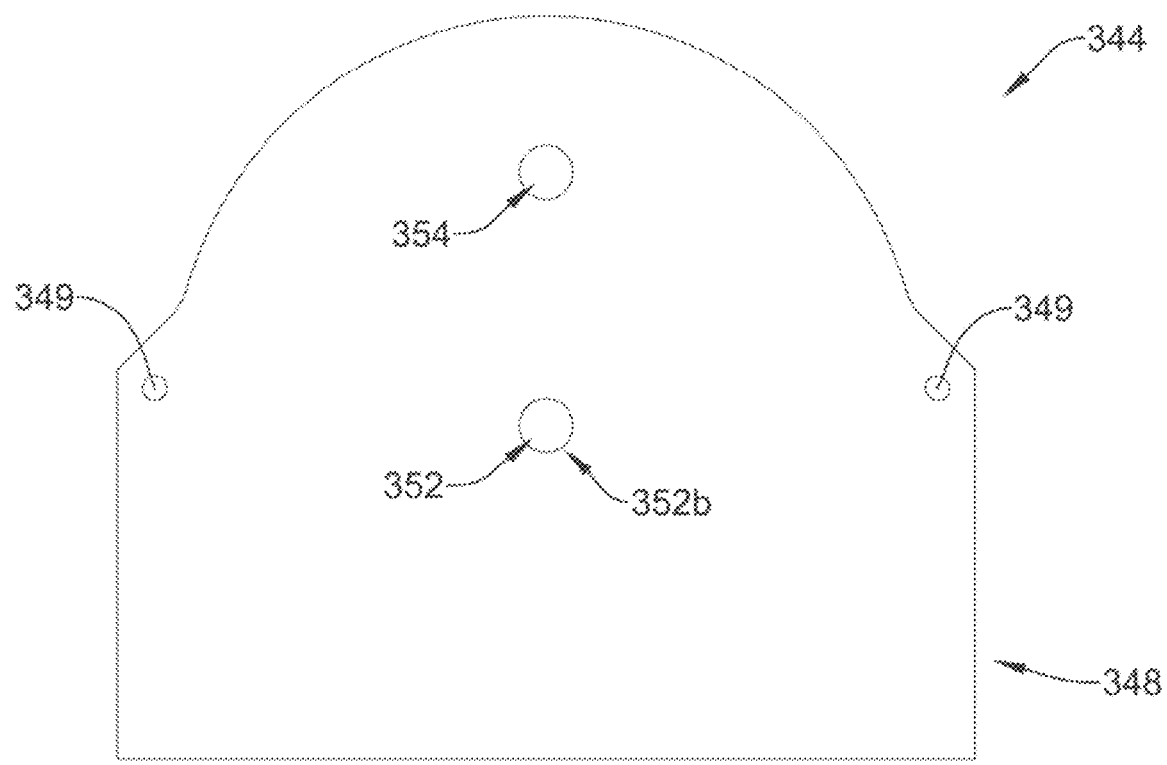
FIG. 20 is a bottom view of the base of a fluid waste container assembly shown in FIG. 14.

FIG. 20 is a bottom view of the base 344 opposite the top view depicted in FIG. 19. The spray opening 352, the drain opening 354, and the holes 349 configured to receive fasteners may extend through the base 344.

Figure 21:
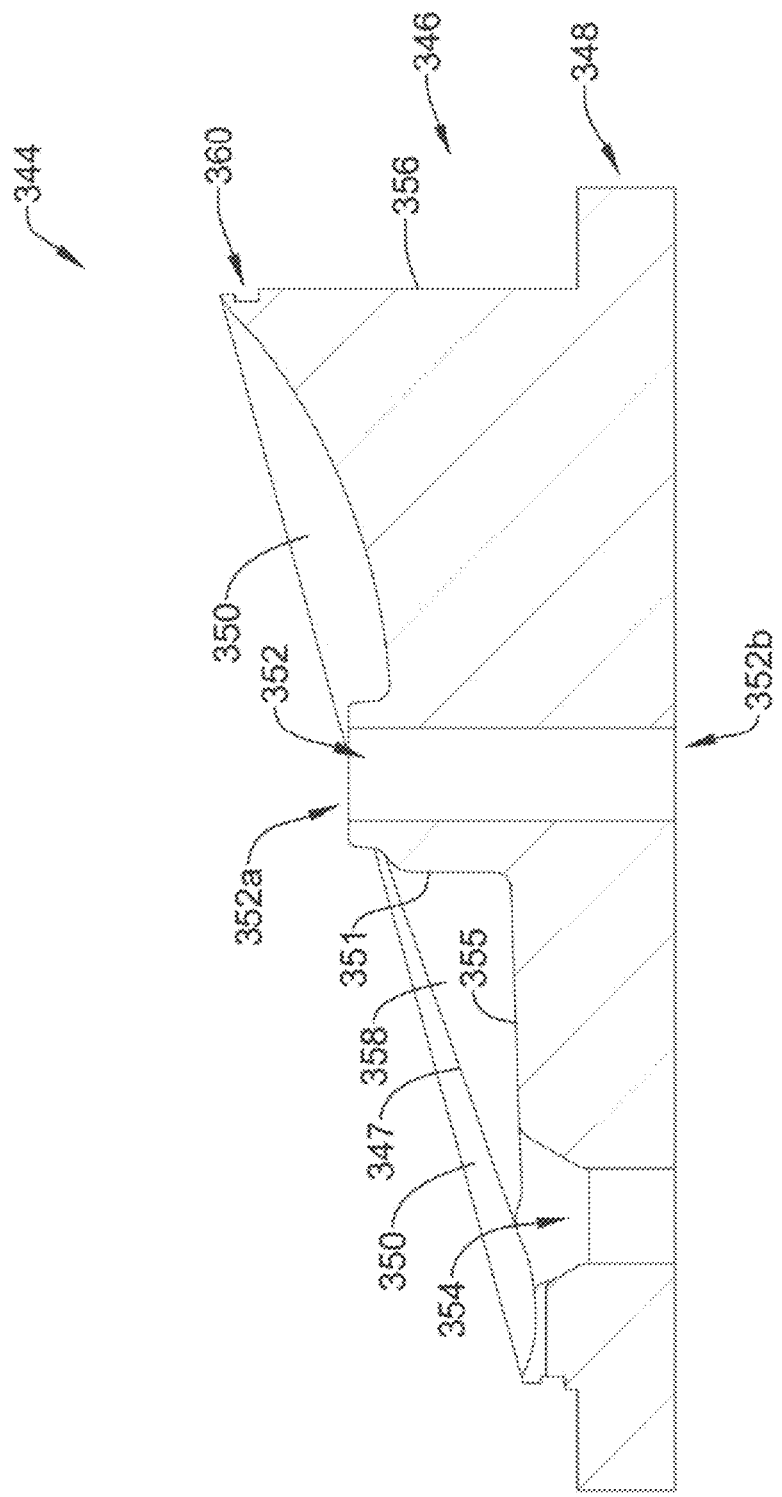
FIG. 21 is a cross-sectional view of the base of a fluid waste container assembly shown in FIG. 14, taken along line 21-21 in FIG. 19.

FIG. 21 a cross-sectional view of the base 344 taken along line 21-21 in FIG. 19. As shown in FIG. 21, the interior surface 350 declines toward the drain opening 354 and extends around the spray opening 352 and the base surface 355. In addition to showing a change in width of the interior surface 350 as it extends toward the drain opening 354, the interior surface 350 may include a non-linear surface (e.g., a rounded surface, as shown in FIG. 21, or other non-linear surface). The non-linear surface may be configured to direct solid medical waste in the container 18 toward a central portion of the interior surface 350 as the surface 350 extends along the path toward the drain opening 354. Such a non-linear surface may facilitate moving solids in collected medical waste away from a body 19 of the container 18 to prevent build up of solids along the body 19 and/or for other benefits.

Figure 22:
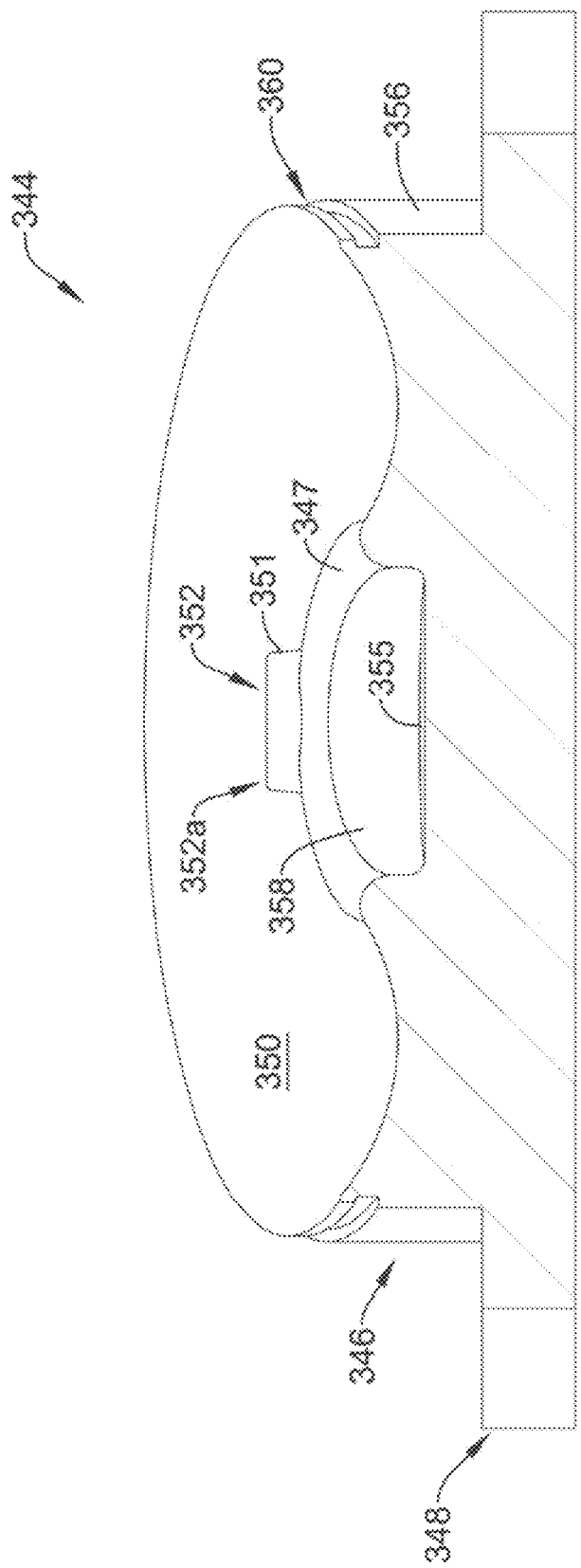
FIG. 22 is a cross-sectional view of the base of a fluid waste container assembly shown in FIG. 14, taken along line 22-22 in FIG. 19.

FIG. 22 is a cross-sectional view of the base 344 taken along line 22-22 in FIG. 19. FIG. 22 shows the interior surface 350 having a width extending between the top of the perimeter wall 356 and the ledge 347. Similar to as in FIG. 21, the interior surface 350 may be non-linear across its width to facilitate preventing build up of solids along the body 19 of the container 18, to direct solid medical waste away from the base surface 355 and a level sensor 57 and toward the drain opening 354, and/or for other benefits.

The base 344 depicted in FIGS. 14-22 may be utilized in the container assembly 17 in a manner similar to that of base 44. As such, when the base 344 is included in a container 18, a top of a path of the interior surface 350 of the base 344 may have a distance to a top of the body 19 of the container 18 that is less than a distance from a bottom of a path (e.g., adjacent the drain opening 354) of the interior surface 350 to a top of the body 19 of the container 18.

Figure 23:
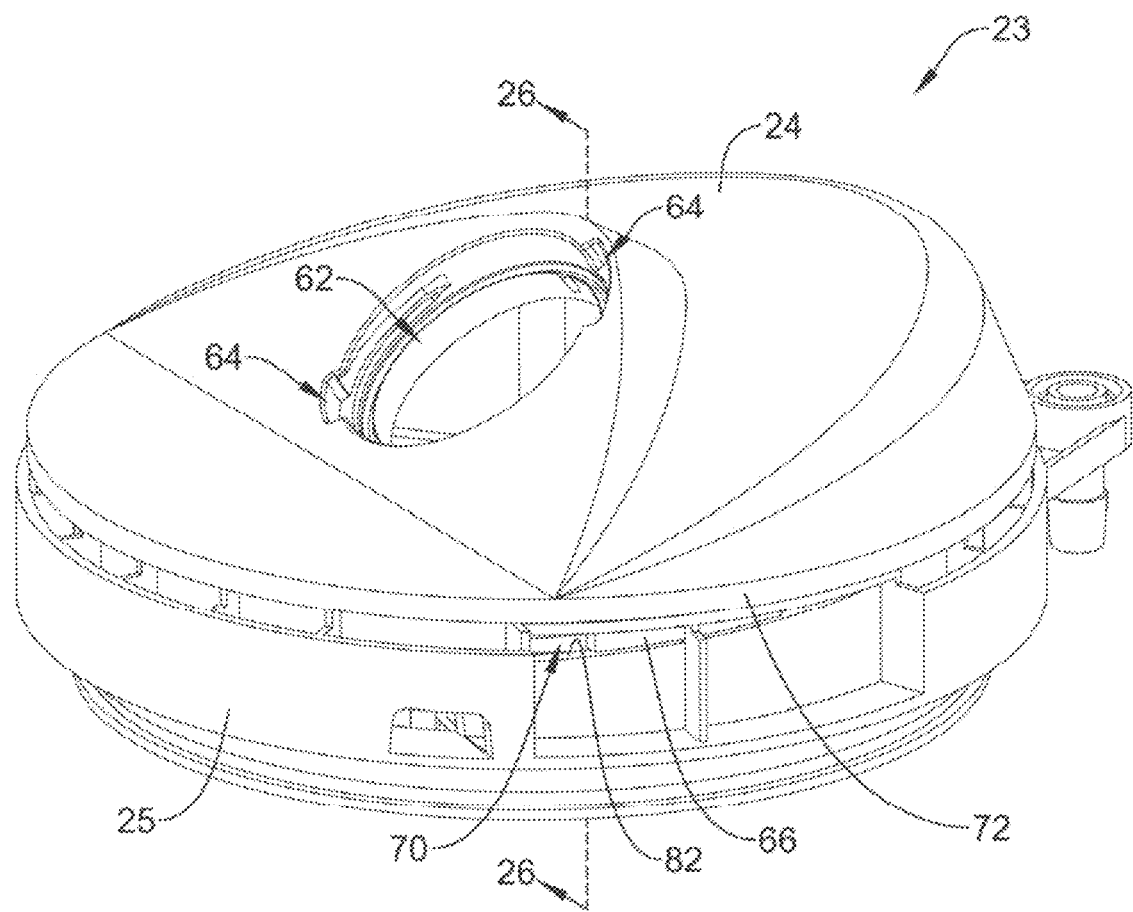
FIG. 23 is a perspective view of a lid assembly of a fluid waste container assembly.

FIG. 23 is a perspective view of the lid assembly 23 of the container assembly 17. The lid assembly 23 may include the lid 24 and the lid ring 25. The lid 24 may include an opening 62 that may be configured to receive a manifold 26. The lid 24 may connect to a manifold inserted into the opening 62 in any manner including, but not limited to, through a friction fit connection, a threaded connection, a bayonet connection, a twist lock connection, and/or one or more other connection mechanisms. In the example shown in FIG. 23, the lid 24 may include one or more tab openings 64 (e.g., two tab openings 64, as shown in FIG. 23) as a part of or extending from the opening 62. The tab openings 64 may be sized and/or otherwise configured to receive tabs extending from sides of the manifold 26 to facilitate a connection between the manifold 26 and the lid 24.

Figure 24:
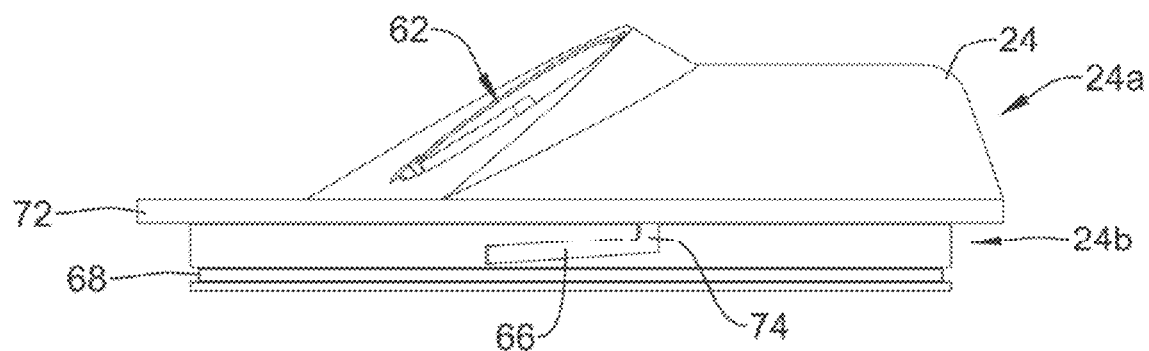
FIG. 24 is a side view of a lid of the lid assembly depicted in FIG. 23.

FIG. 24 is a side view of the lid 24. The lid 24 may have an exterior portion 24a and an interior portion 24b, wherein the exterior portion 24a may be accessible from exterior the cart 10 and the interior portion 24b may be configured to be at last partially received within the lid ring 25. The interior portion 24b may include a locking feature (e.g., a flange 66) for reception in or engagement with a locking feature (e.g., a groove 70) of the lid ring 25, where the locking feature may facilitate engagement of and disengagement of the lid 24 from the container 18 in response to rotation of the lid 24. Optionally, the interior portion 24b of the lid 24 may include an indent 68 for receiving an o-ring that may facilitate creating a hermetic seal between the lid 24 and the lid ring 25.

The lid 24 and the lid ring 25 may engage one another via a lock mechanism utilizing a locking feature on one or more of the lid 24 and the lid ring 25. The lock mechanism between the lid 24 and the lid ring 25 may be any type of locking mechanism configured to releasably connect the lid 24 to the lid ring 25 including a force fit mechanism, a bayonet lock mechanism, a twist lock mechanism, a threaded mechanism, and/or one or more other locking mechanisms. The locking mechanism depicted in the Figures is a twist lock mechanism and the lid 24 may include a flange 66 of or extending from the interior portion 24b. The flange 66 may be configured to engage a groove 70 of or on an interior portion 25b of the lid ring 25.

The flange 66 may have a ramped surface relative to a base 72 of the lid 24, where a distance between the flange 66 and the base 72 decreases in the direction of rotation for engaging the lid 24 with the lid ring 25 (e.g., locking the lid 24 to the lid ring 25). The flange 66 may include a stop 74 and/or a closed end that may engage the lid ring 25 to limit or prevent further rotational movement of the lid 24 in a locking direction.

Figure 25:
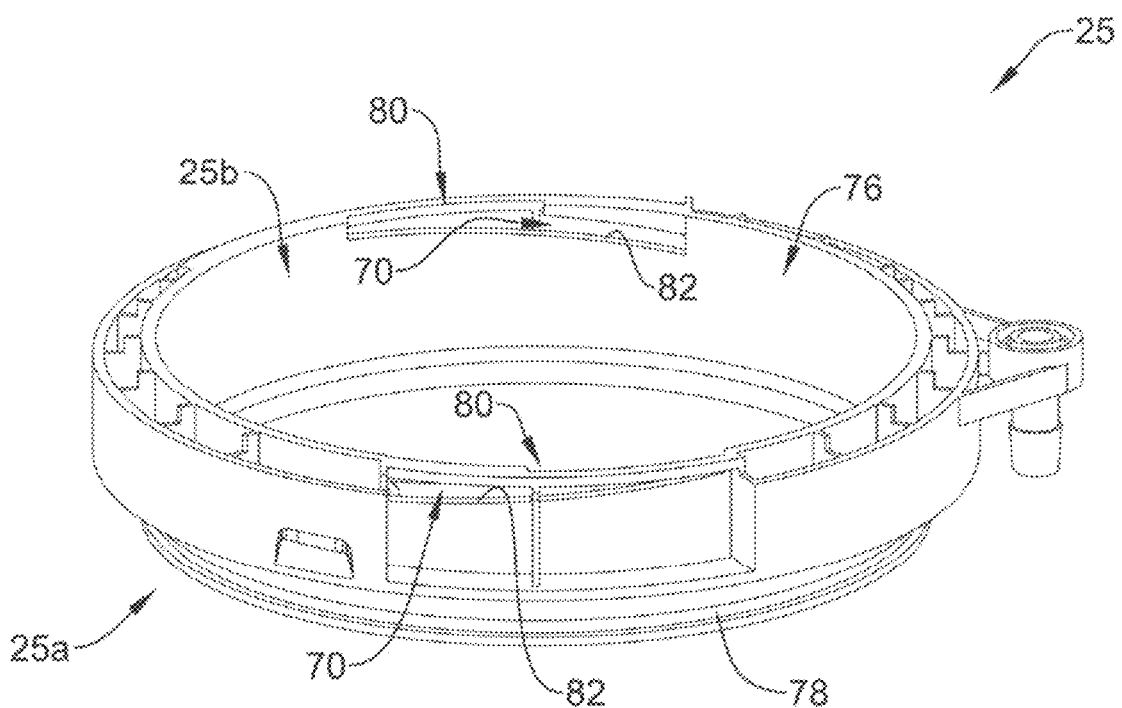
FIG. 25 is a perspective view of a lid ring of the lid assembly depicted in FIG. 23.

FIG. 25 is a perspective view of the lid ring 25. The lid ring 25 includes an exterior portion 25a for engaging the body 19 (e.g., the top end 19b) of the container 18 and an interior portion 25b having and/or defining a central opening 76 into the lumen 19c of the body 19 of the container 18. When the lid 24 is engaged with the lid ring 25, the lid 24 may at least partially cover the central opening 76.

The exterior portion 25a of the lid ring 25 may be sized to fit within a top end of 19b of the body 19. In some cases, the exterior portion 25a of the lid ring 25 may include an indent 78 that may receive an o-ring (not shown). When an o-ring is positioned in the indent 78, the o-ring may facilitate a hermetic seal between the lid ring 25 and the body 19 of the container 18.

The interior portion 25b of the lid ring 25 may include flange openings 80 for receiving flanges of lid 24 in a groove 70 of the lid ring 25 to create a twist lock connection between the lid 24 and the lid ring 25. The twist lock mechanism for engaging the lid 24 with the lid ring 25 may be similar to a bayonet connection, where the lid ring 25 receives the flanges 66 of the lid 24 and twisting the lid relative to the lid ring 25 further engages the lid 24 with the lid ring 25. Additionally, due to the groove 70 having a cam surface 82 and the flange 66 having a ramped surface, a friction fit connection is created to twist lock the lid in place relative to the lid ring 25 after rotational movement of the lid 24 in a locking direction. The lid ring 25 may include a limit 84 that may engage the flange 66 of the lid 24 or other portion of the lid to prevent further rotational movement of the lid 24 in a locking direction.

The separable configuration of the lid assembly 23 (e.g., the twist lock configuration or other connection configuration between the lid 24 and the lid ring 25) may provide access to an interior of the container 18. The configuration of the lid assembly 23 may facilitate gaining access to the interior of the container 18 to remove material from within the container 18 should the drain opening 54 become clogged, should solid material interfere with the level sensor 57 (e.g., a float 59 of a level sensor 57), and/or for one or more other purposes. Although the interior surface 50 of the base 44 may be configured to facilitate directing solids (e.g., bone chips, clots, etc.) in the material within the container 18 toward the drain opening 54 and away from the level sensor 57 (e.g., the float 59 of the level sensor 57), solids may build-up within the container 18 and block the drain opening 54 and/or interfere with the level sensor 57. To unclog the drain opening 54 or remove material from or adjacent to the level sensor 57, the lid 24 of the container assembly 17 may be removed from the lid ring 25 to gain access to the interior of the container 18 and a user may remove material from and/or clean the container 18 to improve the operation of the drain opening 54, the operation of the level sensor 57, and/or an operation of other features of the cart 10.

Figure 26:
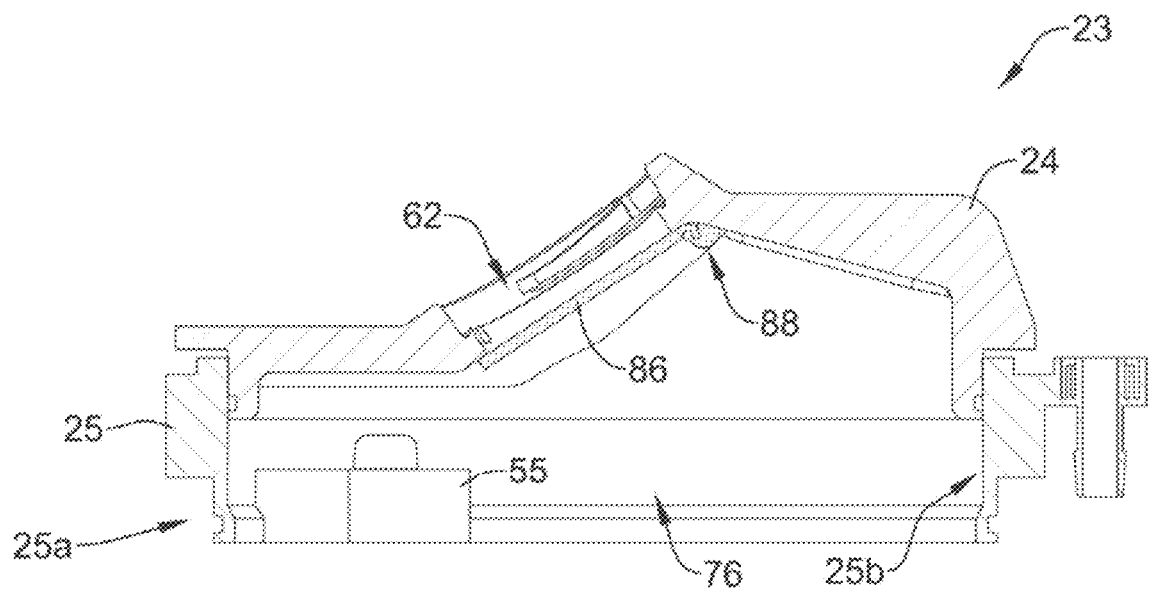
FIG. 26 is a cross-sectional view of the lid assembly in FIG. 23, taken along line 26-26.

FIG. 26 is a cross-section of a lid assembly 23 taken along line 17-17 in FIG. 23. A door 86 is shown closing off or blocking the opening 62 of the lid 24 in FIG. 26. The door 86 may be formed with or connected to the lid 24. In one example, as shown in FIG. 26, the door 86 may be connected to the lid 24 through a living hinge 88 such that the door 86 is a monolithic or unitary portion of the lid 24. However, other hinges and/or connectors may be utilized to connect the door 86 to the lid 24. The hinge 88 may be configured to bias the door 86 to a closed position blocking the opening 62, as shown in FIG. 26.

Figure 27:
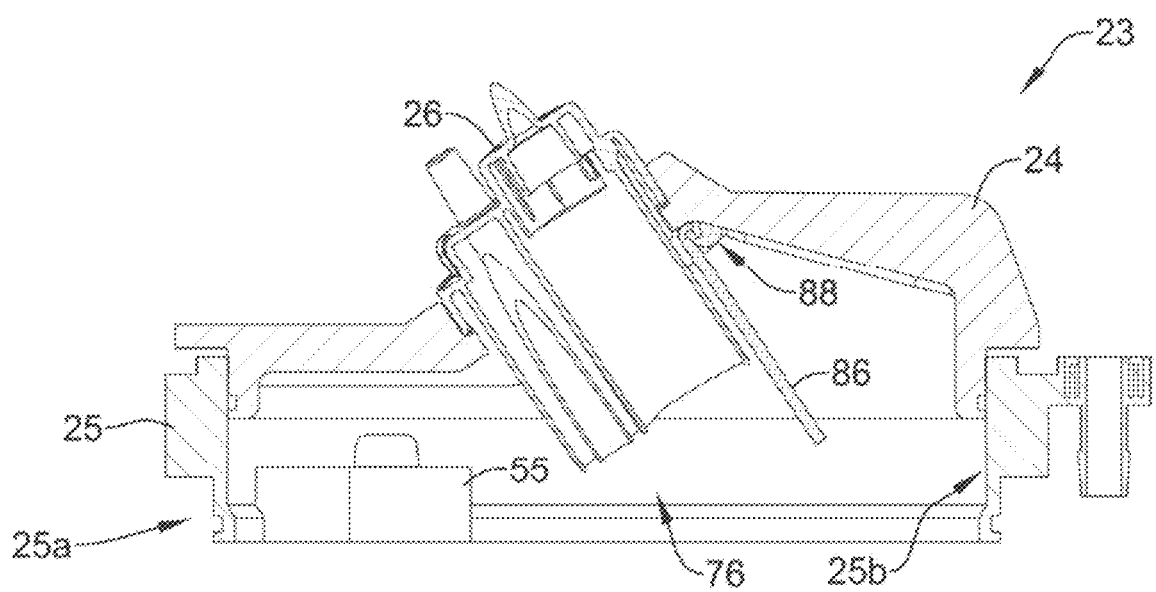
FIG. 27 is a cross-sectional view of a lid assembly with a manifold inserted through an opening in a lid of the lid assembly.

FIG. 27 depicts a cross-section of a lid assembly 23 with a manifold 26 inserted into the opening 62 of the lid 24. As shown in FIG. 27, the door 86 may rotate about the hinge 88 to provide access to the interior of the lid assembly 23 and when the lid assembly is connected to the container 18, provide access to the interior of the container 18. In one example, a manifold 26 may be inserted into the opening 62 in the lid 24. As the manifold 26 is inserted through the opening 62, the manifold 26 may engage and deflect the door 86 to an open position, as shown in FIG. 27. Due, at least in part, to the door 86 being connected to lid 24 with a living hinge 88 biased toward the opening 62, when the manifold 26 is removed from the lid 24 after use or for another purpose the door 86 will return to a closed position blocking the opening 62 in the lid 24.

Figure 28:
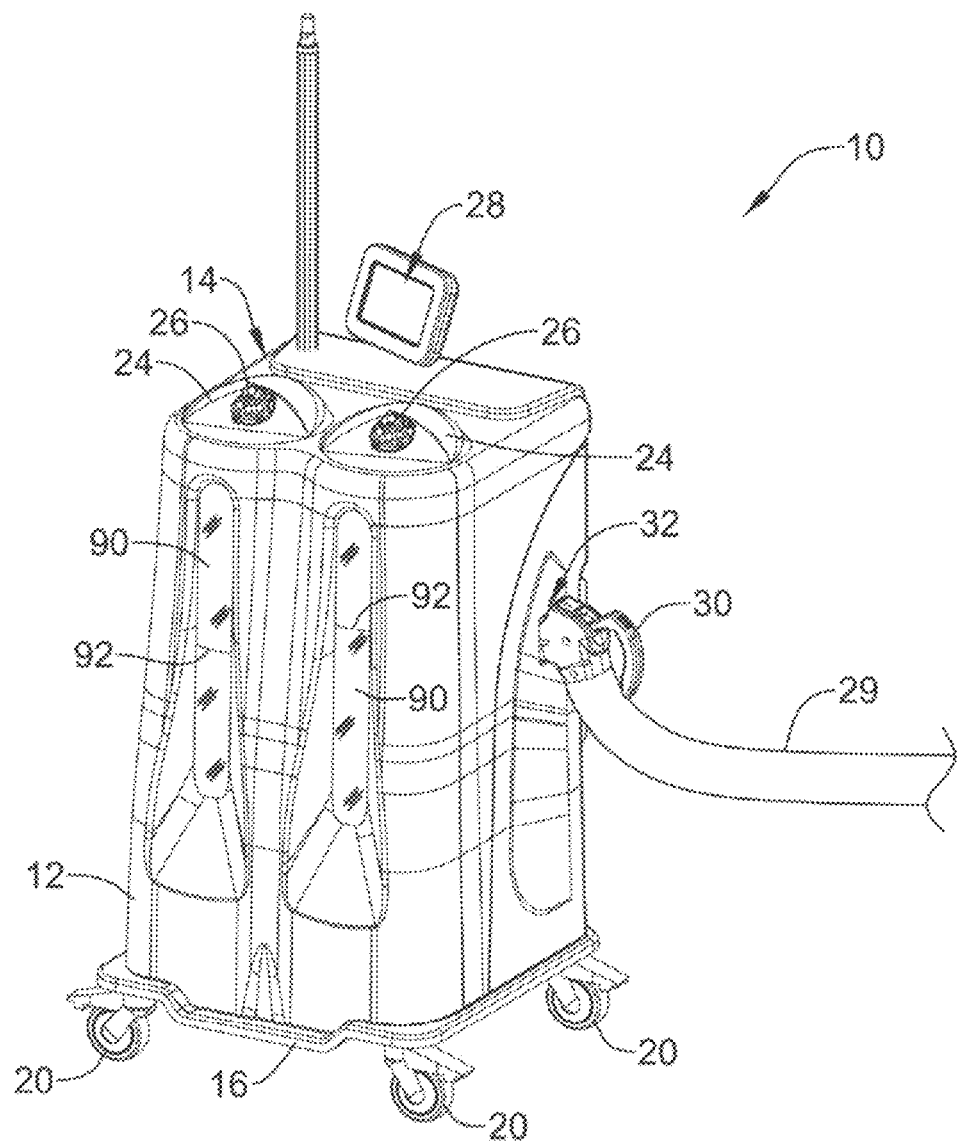
FIG. 28 is a perspective view of a medical waste fluid collection cart.

As discussed, the fluid waste collection cart 10 may collect waste material (mostly fluids, but some solids (e.g., bone chips, clots, etc.) from a surgical site. The collected waste material may be received in the containers 18 within the housing 12 of the fluid waste collection cart 10. From exterior the cart 10, a user may view the material and a level 92 of that material in the containers 18 through windows 90, as shown in FIG. 28. In some cases, for example when the fluid waste collection cart 10 is to be transported between surgical rooms and/or at other times, it may be undesirable to be able to view material in the containers 18.

To facilitate allowing a user to view material in the containers 18 during a procedure and also to facilitate obscuring or covering a view of the material in the containers 18 when it is undesirable to view the material, an actuatable coating may be applied to the windows 90 or body 19 of the containers 18 to obscure a view of the material within the containers 18. Alternatively, or in addition, an actuatable material may be used to make the windows 90 or body 19 of the containers 18 to obscure a view of the material within the containers 18. Thus, when the actuatable coating or material is activated the material within the containers 18 is not viewable from exterior the cart 10, as shown in FIG. 29.

The coating or material used to obscure the windows 90 or body 19 may limit an amount of light (e.g., darken, frost, etc.) that reaches or is reflected from the material in the containers 18. In some instance the coating or material used to obscure the windows 90 or body 19 may be electrically activated and actuated upon activation of a switch. In one example, a switch for activating the coating or material may be tied to a light switch for activating a light that illuminates the material in the containers 18 for viewing. In such cases, when the light switch is activated (i.e., turned on) the coating or material used to obscure the windows 90 or body 19 may be deactivated, allowing visibility to the fluid in the container 18, and when the light switch is deactivated (i.e., turned off), the coating or material used to obscure the windows 90 or body 19 may be activated, obscuring visibility to the fluid in the container 18. Alternatively, or in addition, a switch for actuation of the coating or material may be tied to the controller 100 (e.g., a push button, touch display, etc.) or may be an isolated switch separate from other controls of the cart 10. Alternatively, or in addition, a door may be provided to cover the windows 90 and selectively block a view of the fluid within the containers 18.

Figure 29:
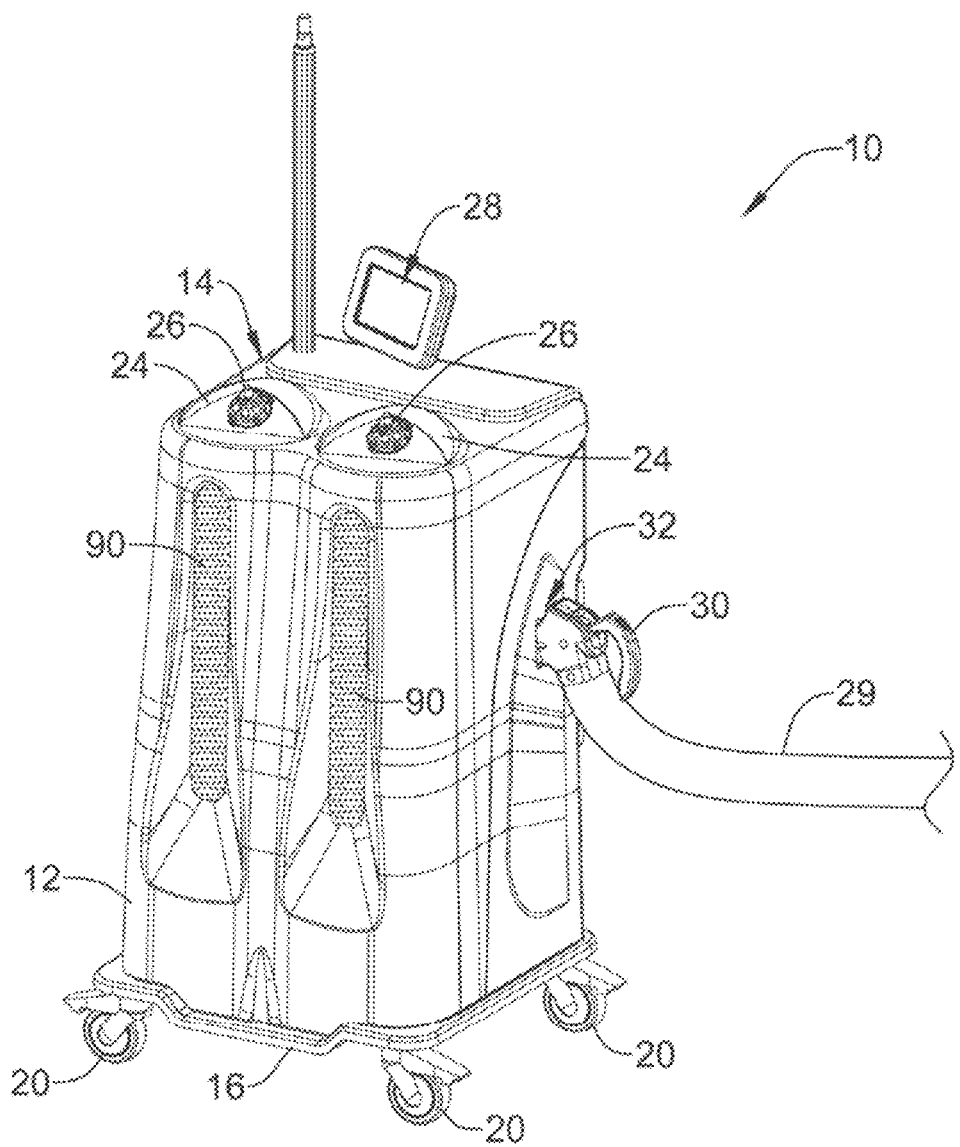
FIG. 29 is a perspective view of a medical waste fluid collection cart.
Figure 30:
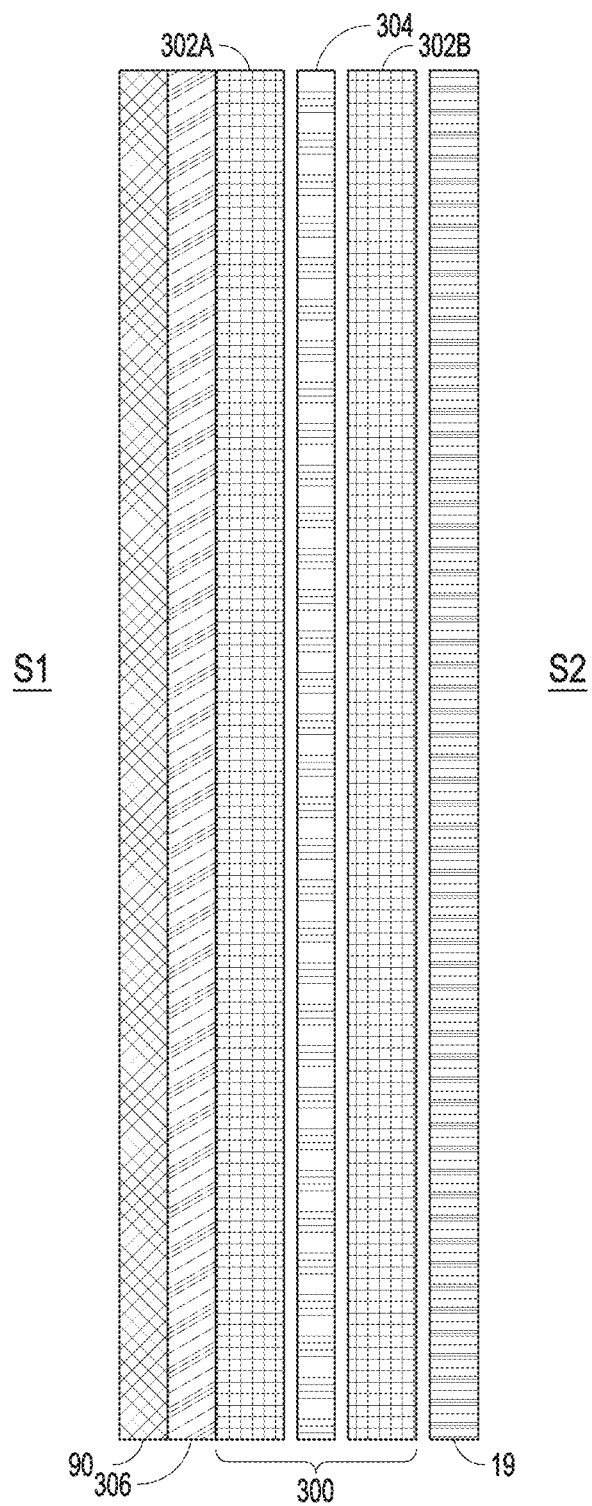
FIG. 30 is a schematic cross-sectional view of a tinting assembly suitable for use in the medical waste fluid collection cart of FIGS. 28 and 29.

FIG. 30 is a schematic cross-sectional view of a tinting assembly 300 suitable for use in the medical waste fluid collection cart 10 of FIGS. 28 and 29.

The tinting assembly 300 can be positioned between the body 19 of the container 18 and the window 90. In the depicted example, the tinting assembly 300 can include film layers 302A and 302B, a polymer dispersed liquid crystal (PDLC) layer 304 and an adhesive layer 306. The adhesive layer 306 can be positioned between window 90 and the tinting assembly 300.

The body 19 of the container 18 can comprise a rigid structure that can support a volume of medical waste, such as various biological fluids, including blood. The body 19 can be made of a material that is clear or transparent to allow light to pass from a first side S1 of the container 18 to a second side S2 of the container 18. The second side S2 of the body 19 can be configured to retain the medical waste, while the first side S1 of the body 19 can be configured to face the environment or the window 90.

The window 90 can be disposed next to an exterior portion of the container 18. For example, the window 90 can be positioned next to the first side S1 of the container 18. The window 90 can also be made of a material that is clear or transparent to allow light to pass from the first side S1 to the second side S2. In various embodiments, the window 90 can be made of plastic or glass.

The tinting assembly 300 can be positioned between the window 90 and the container 18. As such, the tinting assembly 300 can be protected from external environmental conditions by the window 90 and protected from the medical waste by the container 18. However, in other embodiments, a tinting assembly can be incorporated directly into the window 90 or the container 18, or positioned within the container 18 or outside of the window 90. In the depicted embodiment, the tinting assembly 300 is adhered to the interior surface of the window 90 with the adhesive layer 306. The tinting assembly 300 could also be attached to the exterior surface of the container 18.

In the depicted embodiment, the tinting assembly 300 utilizes polymer dispersed liquid crystal (PDLC) layer 304. As is known in the art, PDLCs consist of liquid crystal droplets that are dispersed in a solid polymer matrix. The liquid crystal droplets can be on the order of a few microns in size and react to the application of an electric field. The film layers 302A and 302B can be configured as transparent, conductive layers that act as a capacitor when matrix is disposed therebetween. Power from a power supply, such as from the controller 100 (FIG. 3) can be attached to electrodes on the film layers 302A and 302B.

When no voltage is applied to the electrodes, the liquid crystals are randomly arranged in the droplets, resulting in scattering of light as it passes from the first side S1 to the second side S2. This can result in the tinting assembly 300 having an opaque or semi-transparent appearance. When a voltage is applied across the electrodes, the electric field causes the liquid crystals to align, allowing light to pass through the droplets with very little scattering as the light passes from the first side S1 to the second side S2. Thus, the tinting assembly 300 can have a clear or semi-transparent appearance. The level of transparency can be related to the voltage applied across the electrodes of the film layers 302A and 302B. The voltage applied across the electrodes can be controlled at the controller 100 by an operator of the cart 10.

Tinting apparatus 300 can be activated into a transparent or semi-transparent state in order to allow a surgeon or other medical staff to view the contents of container 18, such as during the performance of a medical procedure or other situations. Thus, the capacity of the container or the condition of the medical waste can be determined. As mentioned previously, the tinting apparatus 300 can be put into an opaque or semi-transparent state to conceal or hide the contents of the body 19 from being visible. The tinting apparatus 300 can remain in such a state in order to prevent viewing of medical waste, which can sometimes have an unpleasant appearance, when a patient is awake or conscious within an operating room, when cart 10 is in a public place, such as a hallway of a hospital, or other situations.

Although described with respect to PDLCs, the tinting assembly 300 can comprise any mechanism that converts between being transparent or semi-transparent in one state and opaque or semi-transparent in another state on demand. The tinting assembly 300 can utilize technologies such as electrochromic, photochromic, thermochromic, suspended particle, micro-blind and polymer dispersed liquid crystal devices to change the appearance of tinting assembly 300 from clear to opaque.

The tinting assembly 300 can comprise a tinting assembly commercially available from Glass Apps, LLC or Smart Tint, Inc., or another commercial supplier of tinting assemblies.

Figure 31:
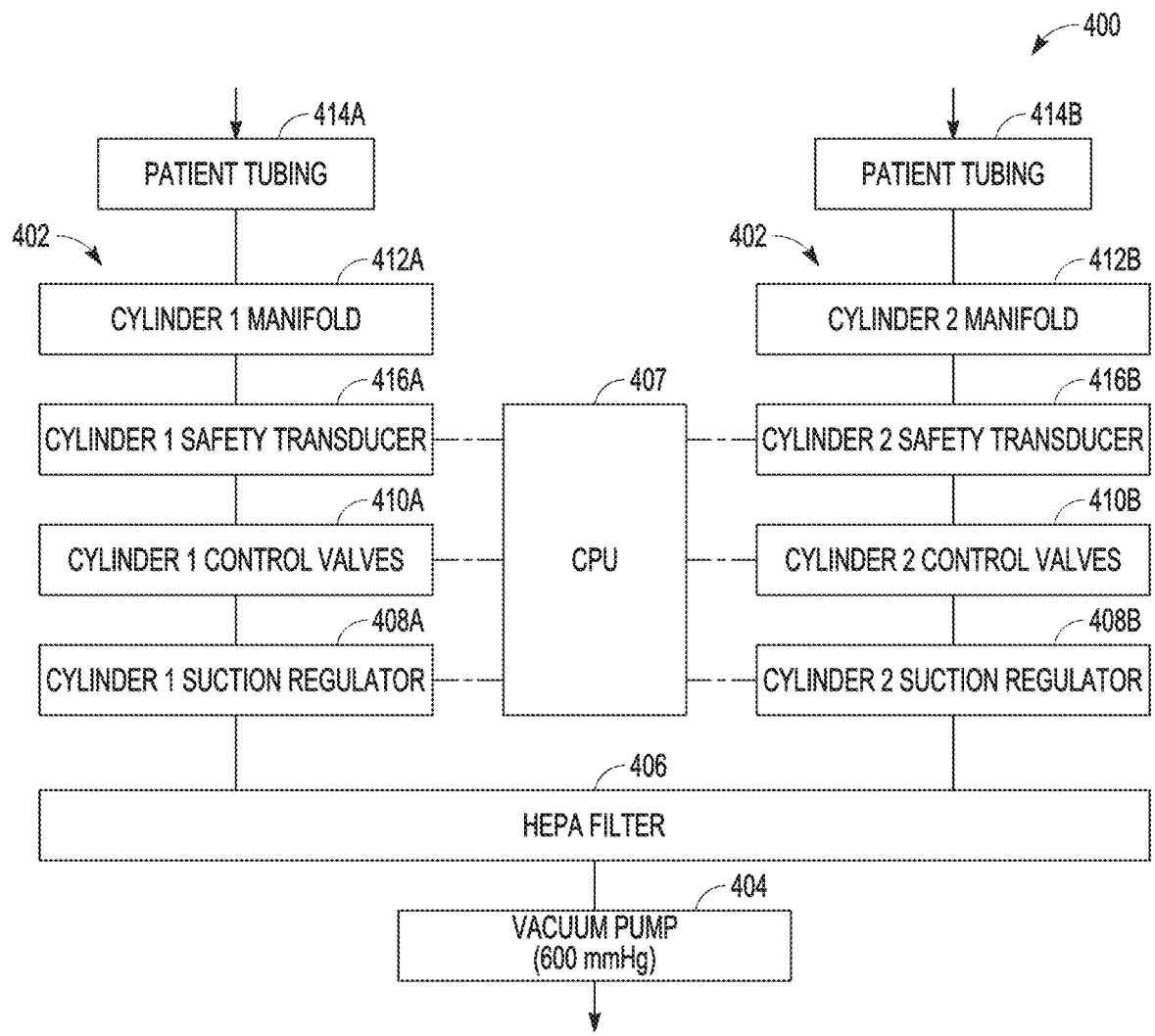
FIG. 31 is a schematic circuit diagram of a secondary vacuum level detection system.

FIG. 31 is a schematic circuit diagram of fluid waste collection system 400 having a secondary vacuum level detection system 402. The system 400 can include a vacuum pump 404, a filter element 406, a processor 407, suction regulators 408A and 408B, control valves 410A and 410B, manifolds 412A and 412B, and tubing 414A and 414B. The secondary vacuum level detection system 402 can include safety transducers 416A and 416B. System 400 can be constructed and operate in a similar fashion as vacuum line system 200 of FIG. 2, with the addition of secondary vacuum level detection system 402.

During operation of the system 400, the vacuum pump 404 can operate to draw vacuums at the tubing 414A and 414B. Fluid from a patient can be drawn into the tubing 414A and 414B and into the manifolds 412A and 412B. Air continues to be drawn into the control valves 410A and 410B, the suction regulators 408A and 408B and the filter element 406 as the vacuum pump 404 generates the suction. Fluid drawn through system 400 and pump 404 is deposited in container 18, as described herein, while passing through manifolds 412A and 412B.

An operator or user of the system 400 can set a desired vacuum level to be achieved at the tubing 414A and 414B via an input at the processor 407, which can be located in the controller 100. The user input can determine the operational state of the control valves 410A and 410B and the suction regulators 408A and 408B. The control valves 410A and 410B and the suction regulators 408A and 408B can operate in a similar manner as valves 206 and suction regulator 214 as described with reference to FIG. 2, above. For example, the vacuum pump 404 can typically run at full power when the system 400 is active, while control valves 410A and 410B are controlled by suction regulators 408A and 408B to reduce the suction or vacuum at the tubing 414A and 414B from full power.

The safety transducers 416A and 416B can directly monitor the vacuum levels at the tubing 414A and 414B. The transducers 416A and 416B can provide a signal to the processor 407 indicating the vacuum levels sensed at the tubing 414A and 414B. The processor 407 can compare the sensed vacuum levels at safety transducers 416A and 416B to the user input provided at the processor 407, which is being controlled by the suction regulators 408A and 408B and the control valves 410A and 410B. The safety transducers 416A and 416B can comprise suitable sensor as is known in the art.

If the sensed vacuum levels are higher than the user selected vacuum levels, the processor 407 can take corrective action. In one example, the processor 407 can generate a user alarm, such as an audio alarm or a visual alarm at the display 28 (FIG. 1). In another example, the processor 407 can adjust the suction regulators 408A and 410B and the control valves 410A and 410B, e.g. to restrict the opening of the control valves 410A and 410B in order to match the sensed vacuum levels to the user selected vacuum level. In another example, the processor 407 can shut-down operation of the system 400 such as by stopping operation of the vacuum pump 404 or closing the control valves 410A and 410B.

Those skilled in the art will recognize that the present disclosure may be manifested in a variety of forms other than the specific embodiments described and contemplated herein. Accordingly, departure in form and detail may be made without departing from the scope and spirit of the present disclosure as described in the appended claims.

What is claimed is:

1. A fluid waste container assembly, comprising:
   a container;
   a window to allow viewing of an interior of the container from an exterior of the container;
   a tinting assembly configured to selectively obscure viewing of the interior of the container, wherein the tinting assembly comprises a layer of tinting material attached to the window to cover an entirety of the window and that can be electronically controlled to selectively change between being opaque to completely obscure visibility into the container through the window and being transparent to allow visibility into the container through the window; and
   a switch electronically connected to the tinting assembly to allow a user to selectively activate the layer of tinting material to control viewing through the window.

2. The fluid waste container assembly of claim 1, further comprising:
   a vacuum pump for producing suction in the container;

a suction regulator for regulating operation of the vacuum pump; and
a vacuum level detection system for sensing a vacuum level generated by the vacuum pump.

3. The fluid waste container assembly of claim 1, further comprising:
a fluid level sensor located at least partially in the container;
wherein the fluid level sensor senses a measure related to an amount of fluid in the container.

4. The fluid waste container assembly of claim 1, further comprising:
a base forming a bottom for the container, the base having an interior surface at least partially defining a drain opening; and
a lid assembly providing selective access to an interior of the container;
wherein the base includes a spray opening at a central location of the base.

5. The fluid waste container assembly of claim 1, wherein the layer of tinting material comprises an actuatable coating or material, wherein actuation of the actuatable coating or material can be controlled by a light switch for activating a light that illuminates the interior of the container, wherein:
the layer of tinting material is controlled to be transparent when the light is on; and
the layer of tinting material is controlled to be opaque when the light is off.

6. The fluid waste container assembly of claim 1, wherein the tinting assembly comprises:
a first film layer; and
a second film layer;
wherein the layer of tinting material is disposed between the first and second film layers.

7. The fluid waste container assembly of claim 6, wherein the layer of tinting material comprises a polymer dispersed liquid crystal (PDLC) layer.

8. The fluid waste container assembly of claim 6, further comprising an adhesive layer attaching the tinting assembly to the fluid waste container assembly.

9. The fluid waste container assembly of claim 6, wherein the window comprises a layer of material positioned against a portion of the container to cover the tinting assembly.

10. The fluid waste container assembly of claim 6, wherein the container and window are fabricated from transparent materials to allow light to pass from the exterior to the interior.

11. The fluid waste container assembly of claim 6, wherein the layer of tinting material is configured to respond to a voltage being applied to the layer of tinting material such that a level of transparency can be varied as the voltage varies.

12. The fluid waste container assembly of claim 11, further comprising electrodes attached to at least one of the first and second film layers to apply the voltage to the layer of tinting material.

13. A medical waste fluid collection system, comprising:
a fluid collection cart including a housing;
a window in the housing;
a container configured to mount within the housing, the container comprising:
a body with a base enclosing a bottom end of the container, the base having a drain opening;
a lid assembly comprising a lid configured to releasably engage the container; and
a tinting material electronically controllable to selectively tint to obscure viewing of contents through substantially all of the window via changing from being transparent to being opaque, wherein the tinting material is adhered to a surface of the window within the housing to completely cover the window; and
a switch electronically connected to the tinting material to allow a user to selectively activate and deactivate the layer of tinting material to control viewing through the window.

14. The medical waste fluid collection system of claim 13, wherein the tinting material comprises a tinting layer, wherein the tinting layer is electronically controllable to selectively change between being opaque to completely obscure visibility into the body of the container through the window and being transparent to allow visibility into the body of the container through the window.

15. The medical waste fluid collection system of claim 14, wherein the tinting layer comprises:
a first film layer of transparent material; and
a second film layer of transparent material;
wherein the tinting layer is disposed between the first and second film layers.

16. The medical waste fluid collection system of claim 15, wherein the tinting layer is adhered to a surface of the window within the housing to completely cover the window.

17. The medical waste fluid collection system of claim 16, wherein the container is at least partially fabricated from a transparent material at the window.

18. The medical waste fluid collection system of claim 14, further comprising:
a controller for operating the medical waste fluid collection system; and
a power supply connected to the tinting layer and the controller;
wherein the switch can be operated by the user to adjust a voltage applied to the tinting layer by the power supply to adjust a level of transparency of the tinting layer.

19. The medical waste fluid collection system of claim 13, wherein the tinting material comprises an actuatable coating or material.

20. The medical waste fluid collection system of claim 19, wherein the coating or material comprises electrochromic, photochromic or thermochromic material.

* * * * *